United States Patent
McCarthy et al.

(10) Patent No.: US 12,004,967 B2
(45) Date of Patent: Jun. 11, 2024

(54) SYSTEMS AND METHODS FOR PLANNING PLACEMENT OF AN ACETABULAR IMPLANT FOR A PATIENT BASED ON PELVIC TILT

(71) Applicant: Howmedica Osteonics Corp., Mahwah, NJ (US)

(72) Inventors: Thomas Francis McCarthy, Neshanic Station, NJ (US); Vincent Libranda Alipit, Tappan, NY (US)

(73) Assignee: Howmedica Osteonics Corp., Mahwah, NJ (US)

( * ) Notice: Subject to any disclaimer, the term of this patent is extended or adjusted under 35 U.S.C. 154(b) by 439 days.

(21) Appl. No.: 17/336,376

(22) Filed: Jun. 2, 2021

(65) Prior Publication Data

US 2021/0369472 A1  Dec. 2, 2021

Related U.S. Application Data

(60) Provisional application No. 63/033,479, filed on Jun. 2, 2020.

(51) Int. Cl.
*A61F 2/00* (2006.01)
*A61F 2/46* (2006.01)
*G16H 30/40* (2018.01)

(52) U.S. Cl.
CPC .......... *A61F 2/4657* (2013.01); *A61F 2/4609* (2013.01); *G16H 30/40* (2018.01); *A61F 2002/4633* (2013.01); *A61F 2002/4668* (2013.01)

(58) Field of Classification Search
None
See application file for complete search history.

(56) References Cited

U.S. PATENT DOCUMENTS

| | | | |
|---|---|---|---|
| 5,880,976 A | 3/1999 | DiGioia, III et al. |
| 5,935,171 A | 8/1999 | Schneider et al. |
| 7,275,218 B2 | 9/2007 | Petrella et al. |
| 7,699,793 B2 | 4/2010 | Gotte et al. |
| 7,877,131 B2 | 1/2011 | Jansen et al. |
| 7,949,386 B2 | 5/2011 | Buly et al. |

(Continued)

FOREIGN PATENT DOCUMENTS

| WO | 2008044679 A1 | 4/2008 |
|---|---|---|
| WO | 2016180438 A1 | 11/2016 |

(Continued)

OTHER PUBLICATIONS

Tao et al., "Gait Analysis Using Wearable Sensors", Feb. 16, 2012, MDPI, Basel, Switzerland (Year: 2012).*

(Continued)

*Primary Examiner* — Naresh Vig
(74) *Attorney, Agent, or Firm* — Howard & Howard Attorneys PLLC

(57) ABSTRACT

Systems and methods are provided for planning placement of an acetabular implant for a patient based on pelvic tilt. The system includes one or more sensors to be placed on the patient to provide measurements of a pelvic tilt angle of the patient taken with the patient in various functional positions to produce patient-specific data based on pelvic tilt from which to plan an inclination angle and a version angle of the acetabular implant for the patient.

19 Claims, 22 Drawing Sheets

(56) References Cited

U.S. PATENT DOCUMENTS

| | | | |
|---|---|---|---|
| 8,400,312 | B2 | 3/2013 | Hotokebuchi et al. |
| 8,469,902 | B2 | 6/2013 | Dick et al. |
| 8,731,253 | B2 | 5/2014 | Dardenne et al. |
| 8,774,900 | B2 | 7/2014 | Buly et al. |
| 9,044,345 | B2 | 6/2015 | Warkentine et al. |
| 9,122,670 | B2 | 9/2015 | Chabanas et al. |
| 9,220,572 | B2 | 12/2015 | Meridew et al. |
| 9,248,002 | B2 | 2/2016 | McCarthy |
| 9,642,572 | B2 | 5/2017 | Mahfouz et al. |
| 9,662,228 | B2 | 5/2017 | McCarthy |
| 9,665,686 | B2 | 5/2017 | Van Vorhis et al. |
| 9,913,691 | B2 | 3/2018 | Brooks |
| 9,916,422 | B2 | 3/2018 | Haimerl |
| 9,924,921 | B1 | 3/2018 | Irish et al. |
| 9,949,797 | B2 | 4/2018 | Meridew et al. |
| 10,314,520 | B2 | 6/2019 | Hauenstein et al. |
| 10,321,961 | B2 | 6/2019 | McCarthy et al. |
| 10,531,924 | B2 | 1/2020 | Kang et al. |
| 11,259,874 | B1* | 3/2022 | Landon ............... G16H 40/67 |
| 2013/0217998 | A1 | 8/2013 | Mahfouz et al. |
| 2014/0276867 | A1* | 9/2014 | Kelley ............... A61B 17/1746 623/22.32 |
| 2014/0378828 | A1* | 12/2014 | Penenberg ............ A61B 6/468 600/424 |
| 2015/0088146 | A1* | 3/2015 | McCarthy .......... A61B 17/1666 606/91 |
| 2015/0106024 | A1 | 4/2015 | Lightcap |
| 2016/0045317 | A1 | 2/2016 | Lang et al. |
| 2016/0157936 | A1 | 6/2016 | Netravali |
| 2016/0206378 | A1 | 7/2016 | Flett et al. |
| 2016/0278868 | A1 | 9/2016 | Berend et al. |
| 2017/0095693 | A1 | 4/2017 | Chang et al. |
| 2017/0119475 | A1 | 5/2017 | McCabe et al. |
| 2017/0128135 | A1* | 5/2017 | McCarthy ............ A61B 5/1121 |
| 2017/0188894 | A1 | 7/2017 | Chang et al. |
| 2017/0202682 | A1 | 7/2017 | McCarthy |
| 2017/0273601 | A1 | 9/2017 | Wang et al. |
| 2017/0367644 | A1 | 12/2017 | Sharman et al. |
| 2018/0125423 | A1 | 5/2018 | Chang et al. |
| 2018/0133551 | A1 | 5/2018 | Chang et al. |
| 2018/0161101 | A1 | 6/2018 | Barsoum et al. |
| 2018/0289313 | A1 | 10/2018 | Inan et al. |
| 2019/0038187 | A1 | 2/2019 | Latella, Jr. |
| 2019/0133693 | A1 | 5/2019 | Mahfouz |
| 2019/0298253 | A1 | 10/2019 | Hal |
| 2020/0046263 | A1 | 2/2020 | Hauenstein et al. |

FOREIGN PATENT DOCUMENTS

| | | | |
|---|---|---|---|
| WO | 2016180439 | A1 | 11/2016 |
| WO | 2019051564 | A1 | 3/2019 |
| WO | 2019068194 | A1 | 4/2019 |
| WO | 2019175899 | A1 | 9/2019 |

OTHER PUBLICATIONS

Bhaskar et al., "Current Concepts in Acetabular Positioning in Total Hip Arthroplasty", Jul.-Aug. 2017, Indian Journal of Orthopaedics (Year: 2017).*

Su et al., "Monocular Vision and IMU-Based System for Prosthesis Pose Estimation During Total Hip Replacement Surgery", Jun. 3, 2017, IEEE Transactions on Biomedical Circuits and Systems, vol. 11, No. 3, Jun. 2017, pp. 661-670 (Year: 2017).*

Barraza-Madrigal, J.A. et al., "Instantaneous Position and Orientation of the Body Segments as an Arbitrary Object in 3D Space by Merging Gyroscope and Accelerometer Information", Articulo De Investigacion, vol. 35, No. 3, Dec. 2014, pp. 241-252.

Berliner, J.L. et al., "What Preoperative Factors Predict Postoperative Sitting Pelvic Position One Year Following Total Hip Arthroplasty? ", Bone Joint J, vol. 100-B, 2018, pp. 1289-1296.

Blondel, B. et al., "Pelvic Tilt Measurement Before and After Total Hip Arthroplasty", Orthopaedics & Traumatology: Surgery & Research, vol. 95, pp. 568-572.

Carollo, PhD, PE, James et al., "Pelvic Tilt in Hip Radiographs can be Estimated Using Anatomical Landmarks to Avoid incorrect Clinical Measurements", ORS Annual Meeting, 2014, 5 pages.

Chen, Eduard et al., "Implant Position Calculation for Acetabular Cup Placement Considering Pelvic Lateral Tilt and Inclination", Computer Aided Surgery, vol. 11, No. 6, Nov. 2006, pp. 309-316.

Dorsavi, ViMove 5.11 User Manual, 2015, 31 pages.

Eggli, S. et al., "The Value of Preoperative Plannign for Total Hip Arthroplasty", The Journal of Bone & Joint Surgery, vol. 80-B, No. 3, May 1998, pp. 381-390.

English language abstract for WO 2008/044679 A1 extracted from espacenet.com database on Jun. 7, 2021, 2 pages.

Esposito, PhD, Christina I., "Does Degenerative Lumbar Spine Disease Influence Femoracetabular Flexion in Patients Undergoing Total Hip Arthroplasty?", Clin Orthop Relat Res, vol. 474, 2016, pp. 1788-1797.

Fischer, Maxmilian C.M. et al., "Relationship Between Pelvic Morphology and Functional Parameters in Standing Position for Patient-Specific Cup Planning in THA", Epic Series in Health Sciences, vol. 1, 2017, pp. 88-92.

Goujon-Pillet, PhD, et al., "Three-Dimensional Motions of Trunk and Pelvis During Transfemoral Amputee Gait", Arch Phys Med Rehabil, vol. 89, Jan. 2008, pp. 87-94.

Imai, MD, Norio et al., "Pelvic Flexion Measurement From Lateral Projection Radiographs is Clinically Reliable", Clin Orthop Rrlated Res, vol. 471, pp. 1271-1276.

Inaba, Yutaka et al., "Preoperative Planning for Implant Placement With Consideration of Pelvic Tilt in Total Hip Arthroplasty: Postoperative Efficacy Evaluation", BMC Muscoskeletal Disorders, vol. 17, 2016, 7 pages.

Kok, Manon et al., "Using Inertial Sensors for Position and Orientation Estimation", Foundations and Trends in Signal Processing, vol. 11, No. 1-2, 2017, 90 pages.

Lazennec, J.Y. et al., "Pelvis and Total Hip Arthroplasty Acetabular Component Orientations in Sitting and Standing Positions: Measurements Reproducibility with EOS Imaging System Versus Conventional Radiographies", Orthopaedics & Traumatology: Surgery & Research, vol. 97, 2011, pp. 373-380.

Lazennec, J.Y., "Lumbar-Pelvic-Femoral Balance on Sitting and Standing Lateral Radiographs", Orthopaedics & Traumatology: Surgery and Research, vol. 99S, 2013, pp. S87-S103.

Luinge, H.J. et al., "Measuring Orientation of Human Body Segments Using Miniature Gyroscopes and Accelerometers", Med. Biol. Eng. Comput., vol. 43, 2005, pp. 273-282.

Maratt, MD, Joseph D., et al., "Pelvic Tilt in Patients Undergoing Total Hip Arthroplasty: When Does it Matter?", The Journal of Arthroplasty, vol. 30, 2015, pp. 387-391.

Mjosund, Hanne Leirbekk et al., "Clinically Acceptable Agreement Between the ViMove Wireless Motion Sensor System and the Vicon Motion Capture System When Measuring Lumbar Region Inclination Motion in the Sagittal and Coronal Planes", BMC Muscoskeletel Disorders, vol. 18, 2017, 9 pages.

Moes, C.C.M., M.Sc., "Measuring the Tilt of the Pelvis", Oct. 19, 1999, 20 pages.

Parcells, Bert, "Cup Placement", Hip and Knee Book, Mar. 1, 2017, 9 pages.

Pierrepont, J. et al., "Patient-Specific Component Alignment in Total Hip Arthroplasty", Reconstructive Review, vol. 6, No. 4, Dec. 2016, 11 pages.

Pierrepont, J. et al., "Variation in Functional Pelvic Tilt in Patients Undergoing Total Hip Arthroplasty", Bone Joint J, vol. 99-B, 2017, pp. 184-191.

Posteraro, Robert H., "A PACS Education Presentation", Scholar Archive, vol. 191, 2003, 256 pages.

Snijders, MD, T.E. et al., "Trigonometric Algorithm Defining the True Three-Dimensonal Acetabular Cup Orientation", The Journal of Bone and Joint Surgery, 2018, 9 pages.

Sprigle, PhD, Stephen et al., "Development of a Noninvasive Measure of Pelvic and Hip Angles in Seated Posture", Arch Phys Med Rehabil, vol. 83, Nov. 2002, 6 pages.

Stryker, "MAKO THA Application User Guide", 2020, 172 pages.

Stryker, "MAKO THA Surgical Guide", PN 214408, Rev 1, Jun. 2019, 82 pages.

(56) References Cited

OTHER PUBLICATIONS

Tamura, Satoru et al., "Hip Range of Motion During Daily Activities in Patients With Posterior Pelvic Tilt from Supine to Standing Position", Journal of Orthopaedic Research, Apr. 2014, pp. 542-547.

Tannast, M. et al., "Estimation of Pelvic Tilt on Ateroposterior X-Rays—A Comparison of Six Parameters", Skeletal Radiol, vol. 35, 2006, pp. 149-155.

Tetsunaga, Tomonori et al., "An Accelerometer-Based Navigation System Provides Acetabular Cup Orientation Accuracy Comparable to that of Computed Tomography-Based Navigation During Total Hip Arthroplasty in the Supine Position", Journal of Orthopaedic Surgery and Research, 2020, 7 pages.

Tyler, Timothy et al., "A New Pelvic Tilt Detection Device: Roentgenographic Validation and Application to Assessment of Hip Motion in Professional Ice Hockey Players", JOSPT, vol. 24, No. 5, Nov. 1996, pp. 303-309.

Wang, R.Y. et al., "Measurement of Acetabular Inclination and Anteversion via CT generated 3D Pelvic Model", BMC Musculoskeletal Disorders, vol. 18, 2017, 7 pages.

Yang, MD, Guoyue et al., "The Influence of Pelvic Tilt on the Anteversion Angle of the Acetabular Prosthesis", Orthopaedic Surgery, 2019, pp. 762-769.

Yi, Chunzhi et al., "Estimating Three-Dimensional Body Orientation Based on an Improved Complementary Filter for Human Motion Tracking", Sensors, vol. 18, No. 3765, 2018, 19 pages.

Zhang, Yuxin et al., "Electronic Skin Wearable Sensors for Detecting Lumbar-Pelvic Movements", Sensors, vol. 20, No. 1510, 2020, 28 pages.

\* cited by examiner

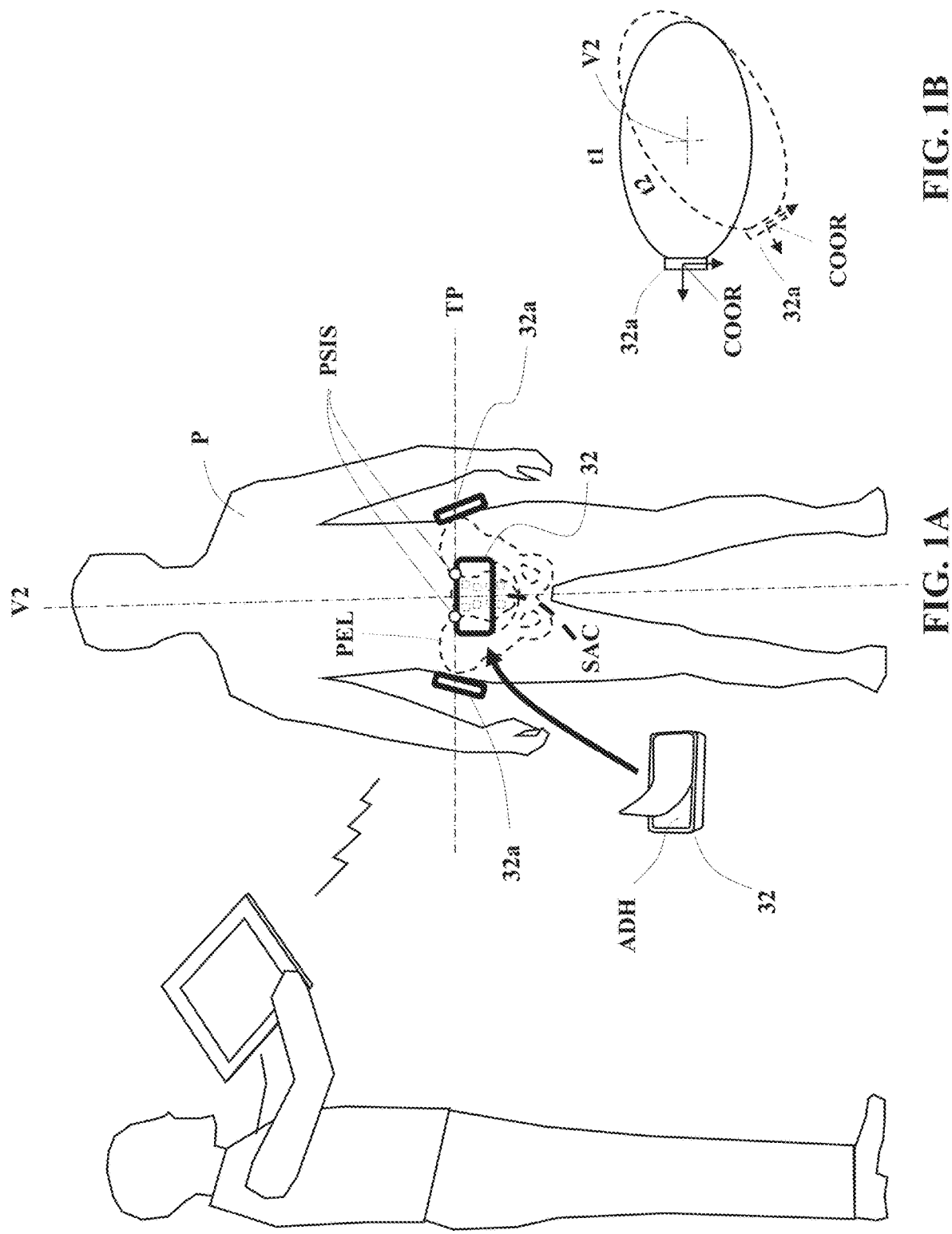

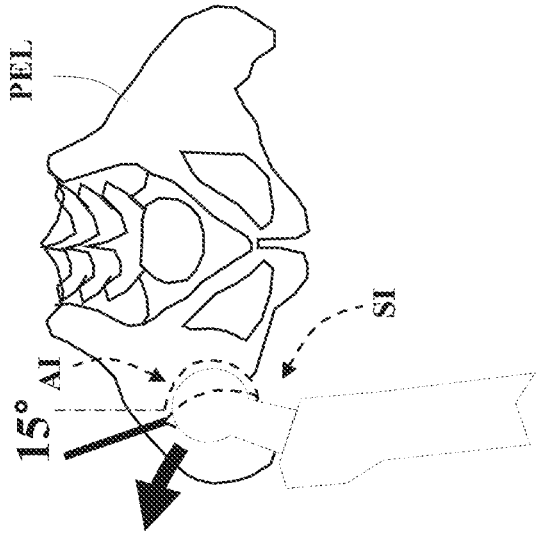
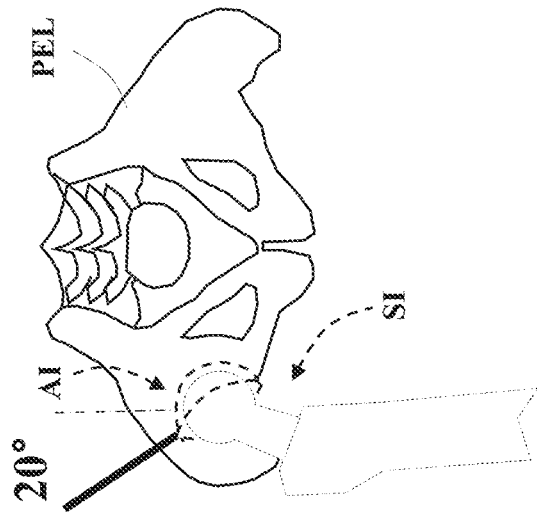
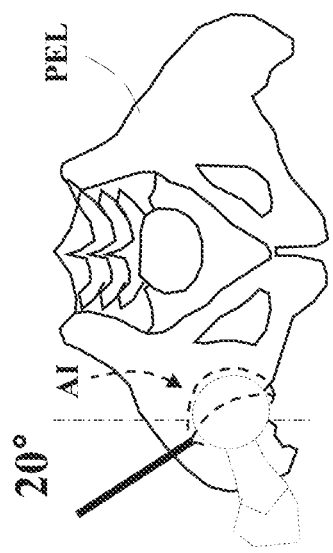
FIG. 3A

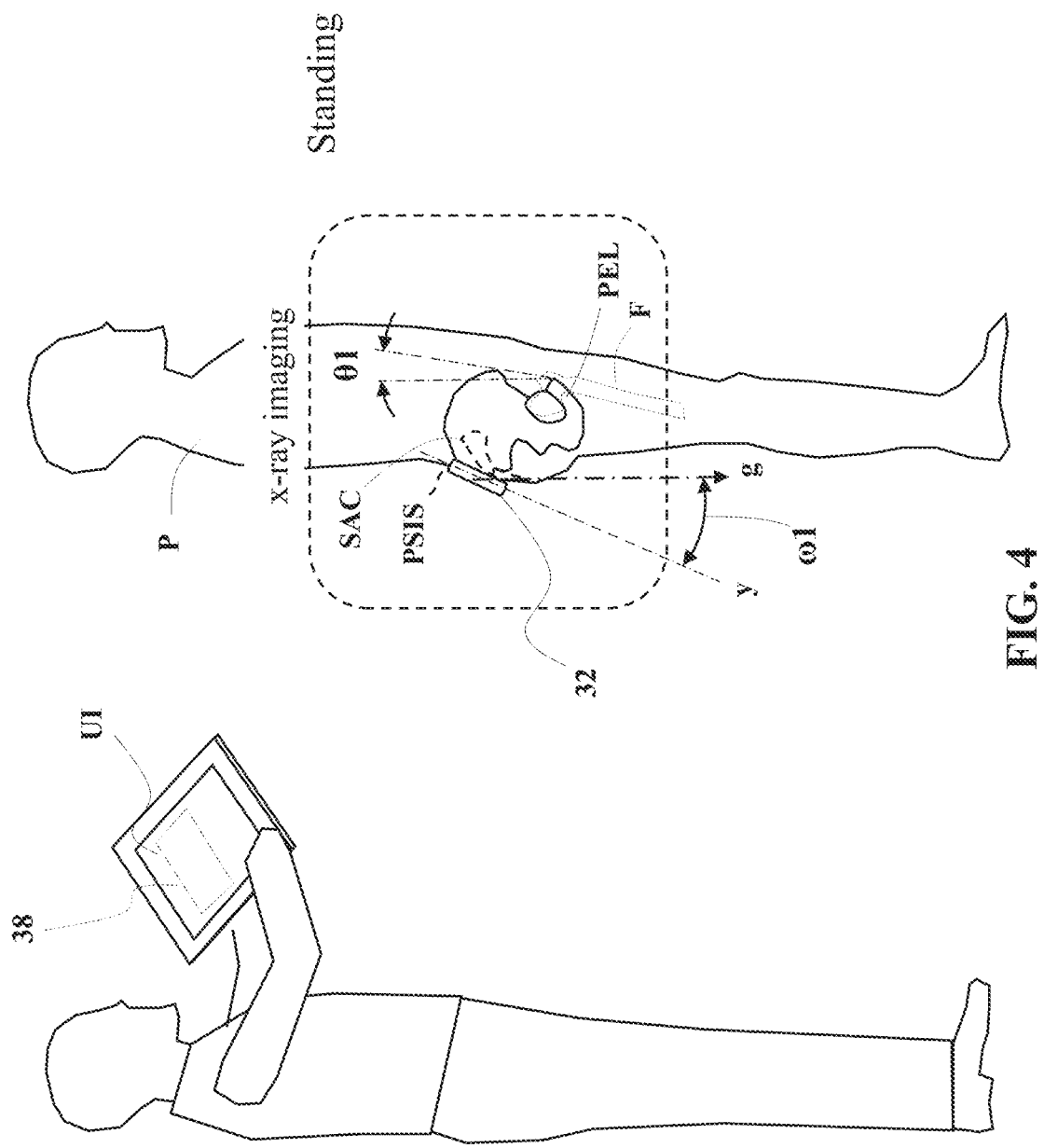

SYSTEMS AND METHODS FOR PLANNING PLACEMENT OF AN ACETABULAR IMPLANT FOR A PATIENT BASED ON PELVIC TILT

CROSS-REFERENCE TO RELATED APPLICATIONS

This application claims priority to and the benefit of U.S. Provisional Patent Application No. 63/033,479, filed on Jun. 2, 2020, the disclosure of which is expressly incorporated by reference in its entirety.

TECHNICAL FIELD

The present disclosure relates generally to systems and methods for planning placement of an acetabular implant for a patient based on pelvic tilt.

BACKGROUND

Total hip arthroplasty (THA) involves replacement of a patient's hip joint with artificial implants, including placement of an acetabular implant in the patient's pelvis. Surgeons often make judgement calls on how best to place the acetabular implant within the pelvis. A well-placed acetabular implant will avoid impingement by a corresponding stem implant as impingement can lead to hip dislocation. In the past, a proposed "safe zone" that could be targeted for placement is one in which the acetabular implant is placed with 40° (+/−10°) inclination and 15° (+/−10°) anteversion.

Recent publications of clinical data have shown that dislocations occur within the bounds of this "safe zone." Accordingly, some surgeons and researchers believe that there should be patient-specific targets for placement of the acetabular implant as individual patients have different levels of mobility and move in different ways. Ideally, placement of the acetabular implant will account for all motions and avoid impingement and dislocation during activities known to be causes of dislocation, such as squatting, picking up an object from a floor, getting out of a chair, and pivot and turn motions.

The pelvis plays a major role in analysis of a patient's movement as it naturally flexes forward and backward during certain motions. A placement of the acetabular implant to avoid dislocation would be different for a pelvis that is stiff versus one that is highly flexible. Thus, data regarding pelvic motion for each patient can be helpful in determining how best to place the acetabular implant. However, obtaining data on pelvic motion currently includes obtaining multiple radiographic images, which could include CT scans, A/P x-ray imaging, and lateral x-ray imaging, which exposes the patient to additional radiation. It is desirable to minimize radiation associated with imaging, but at the same time obtain suitable, patient-specific data of the pelvis to determine how best to place the acetabular implant.

SUMMARY

A system is provided for planning placement of an acetabular implant for a patient based on pelvic tilt. The system includes one or more sensors to be placed on the patient. The one or more sensors are operable to provide a first measurement taken with the patient in a first functional position to establish an initial sensor tilt angle. The one or more sensors are also operable to provide a second measurement taken, in an image-free mode, with the patient in a second functional position, different than the first functional position, to produce patient-specific data based on pelvic tilt from which to plan an inclination angle and a version angle of the acetabular implant for the patient. The system also includes a system controller operable to establish an image-based pelvic tilt angle for the patient for the first functional position and correlate the initial sensor tilt angle to the image-based pelvic tilt angle.

A method is provided for planning placement of an acetabular implant for a patient based on pelvic tilt. The method includes establishing an image-based pelvic tilt angle for the patient for a first functional position. A first measurement is provided by one or more sensors placed on the patient and taken with the patient in the first functional position to establish an initial sensor tilt angle. The initial sensor tilt angle is correlated to the image-based pelvic tilt angle. A second measurement is provided by the one or more sensors placed on the patient and taken, in an image-free mode, with the patient in a second functional position, different than the first functional position, to produce patient-specific data based on pelvic tilt from which to plan an inclination angle and a version angle of the acetabular implant for the patient.

BRIEF DESCRIPTION OF THE DRAWINGS

Advantages of the present disclosure will be readily appreciated as the same becomes better understood by reference to the following detailed description when considered in connection with the accompanying drawings.

FIG. 1A illustrates positioning of sensors on a patient.

FIG. 1B illustrates rotation or twisting of the patient being measured by a pelvic sensor.

FIG. 3A illustrates a patient with stiff spinopelvic mobility.

FIG. 4 illustrates a user taking one or more initial measurements with a sensor while a patient is in a standing position.

DETAILED DESCRIPTION

Figure 1:
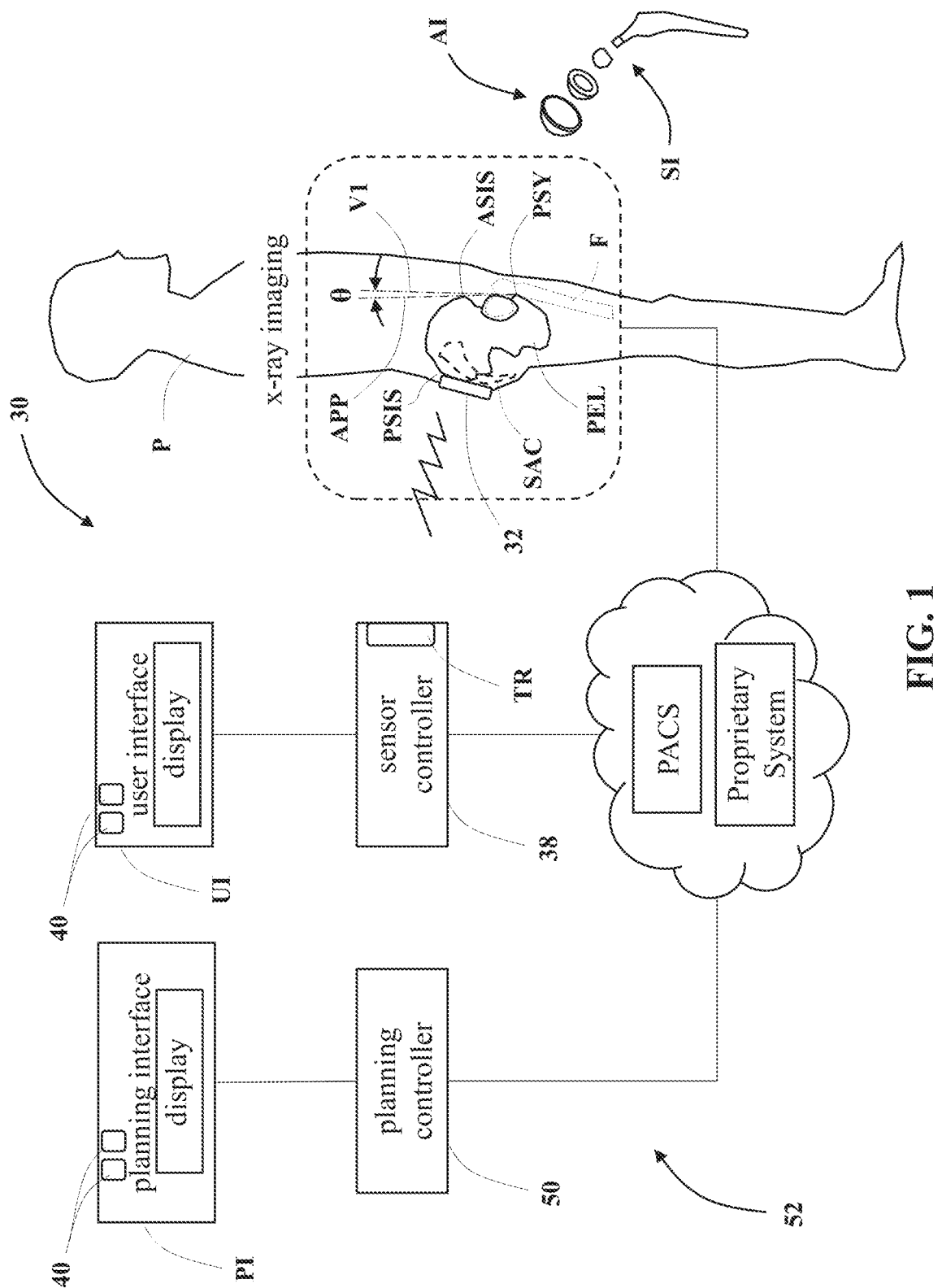
FIG. 1 is a schematic view of a system for obtaining measurements of pelvic tilt.

Referring to FIG. 1, a system 30 is shown for planning placement of an acetabular implant AI for a patient P based on pelvic tilt. During a total hip arthroplasty (THA) procedure, the acetabular implant AI is placed in a pelvis PEL of the patient P, while a stem implant SI is placed in a femur F of the patient P. The acetabular implant AI may include a shell/cup (and often, an insert/liner), while the stem implant SI may include a stem and a femoral head. Stemless implants may also be used for the femur F. Collectively, the acetabular implant AI and the stem implant SI form a replacement hip joint for the patient P. When planning how best to place the acetabular implant AI for the THA procedure, a surgeon considers patient-specific data regarding the individual patient's anatomy and mobility. Such patient-specific data is provided by the system 30.

The system 30 comprises one or more sensors to be placed on the patient P, including one or more pelvic sensors 32. Each pelvic sensor 32 is operable to provide a plurality of measurements that are helpful in planning placement of the acetabular implant AI. In some versions, one pelvic sensor 32 is adapted to be placed on a back of the patient P (on the patient's skin) adjacent to posterior superior iliac spines (PSISs) and/or a sacrum SAC of the patient P to measure a pelvic tilt angle θ of the pelvis PEL. The posterior superior iliac spines (PSISs) and/or the sacrum SAC are externally palpable to facilitate placement of the pelvic sensor 32. In some cases, the sacrum SAC may be more readily palpable, such as when the patient P has a high body mass index (BMI) and additional soft tissue covers the posterior superior iliac spines (PSISs) making them more difficult to locate. The sacrum SAC is a suitable reference location for placement of the pelvic sensor 32, since the sacrum SAC moves in concert with the pelvis PEL. The pelvic tilt angle θ is defined by reference to an anterior pelvic plane (APP), which connects anterior superior iliac spines (ASISs) and a pubic symphysis (PSY)(or pubic tubercles) of the patient P (see also FIG. 1C). The pelvic tilt angle θ, in the versions shown herein, is the angle between the anterior pelvic plane (APP) and a vertical line V1 (e.g., defined relative to gravity) but could be defined differently in other versions.

Referring to FIG. 1A, the pelvic sensor 32 may be placed on the patient P at any suitable location to measure the pelvic tilt angle θ. A line may be drawn on the patient's back connecting the posterior superior iliac spines (PSISs) and the pelvic sensor 32 placed just below this line and horizontally centered thereon in the area of the sacrum SAC. Alternatively, after finding the sacrum SAC on the patient P, the pelvic sensor 32 may be placed at any suitable location on the patient's back adjacent the sacrum SAC so that the pelvic sensor 32 moves with the sacrum SAC (and by extension, with the pelvis PEL) during the patient's movement.

Additionally, or alternatively, one or more pelvic sensors 32a may be positioned on a side of the patient P, adjacent to the pelvis PEL of the patient P. In some versions, a single pelvic sensor 32a may be used to measure rotation or twisting of the pelvis PEL by establishing an initial pose of the pelvic sensor 32a at a first time t1 (e.g., zero pose), asking the patient P to rotate or twist their pelvis PEL, and then taking a second measurement at a second time t2 after the rotation or twisting is complete to determine a second pose of the pelvic sensor 32a. Thereafter, the rotation or twisting may be calculated as the angular difference between the two poses with respect to one or more reference axes and/or reference planes of the pelvic sensor 32a. FIG. 1B illustrates the pose of a coordinate reference frame COOR of the pelvic sensor 32a changing between the initial pose at the time t1 and the second pose at the time t2. In some versions, two pelvic sensors 32a may be positioned on the patient P, one on each side, adjacent to the pelvis PEL of the patient P. The one or more pelvic sensors 32a may measure rotation or twisting of the pelvis PEL of the patient P in one or more planes of the patient P. For instance, the one or more pelvic sensors 32a may be capable of measuring rotation or twisting of the pelvis PEL about a vertical axis V2 placed centrally through the patient P and in a transverse plane TP, located perpendicular to the vertical axis V2. It is also contemplated that the one or more pelvic sensors 32a may be capable of measuring rotation or twisting of the pelvis PEL in other ways, including relative to other reference axes and/or reference planes of the pelvic sensor 32a and/or of the patient P.

The pelvic sensors 32, 32a are attached to the patient P in a non-invasive manner to avoid tissue injury. The pelvic sensors 32, 32a may be attached to the skin of the patient P via adhesive, tape, bands, straps, or other suitable method of attachment. FIG. 1A shows the pelvic sensor 32 before and after attachment to the patient's skin. To place the pelvic sensor 32 on the patient's skin, a backing is first peeled off and removed from the pelvic sensor 32 to reveal adhesive ADH on the pelvic sensor 32 that mounts the pelvic sensor 32 to the patient's skin. The two pelvic sensors 32a may be identical to the pelvic sensor 32. As a result, only the pelvic sensor 32 and its components and functions will be described in detail herein, but such description is equally applicable to the two pelvic sensors 32a. Additional sensors and measurements are also contemplated.

Figure 1C:
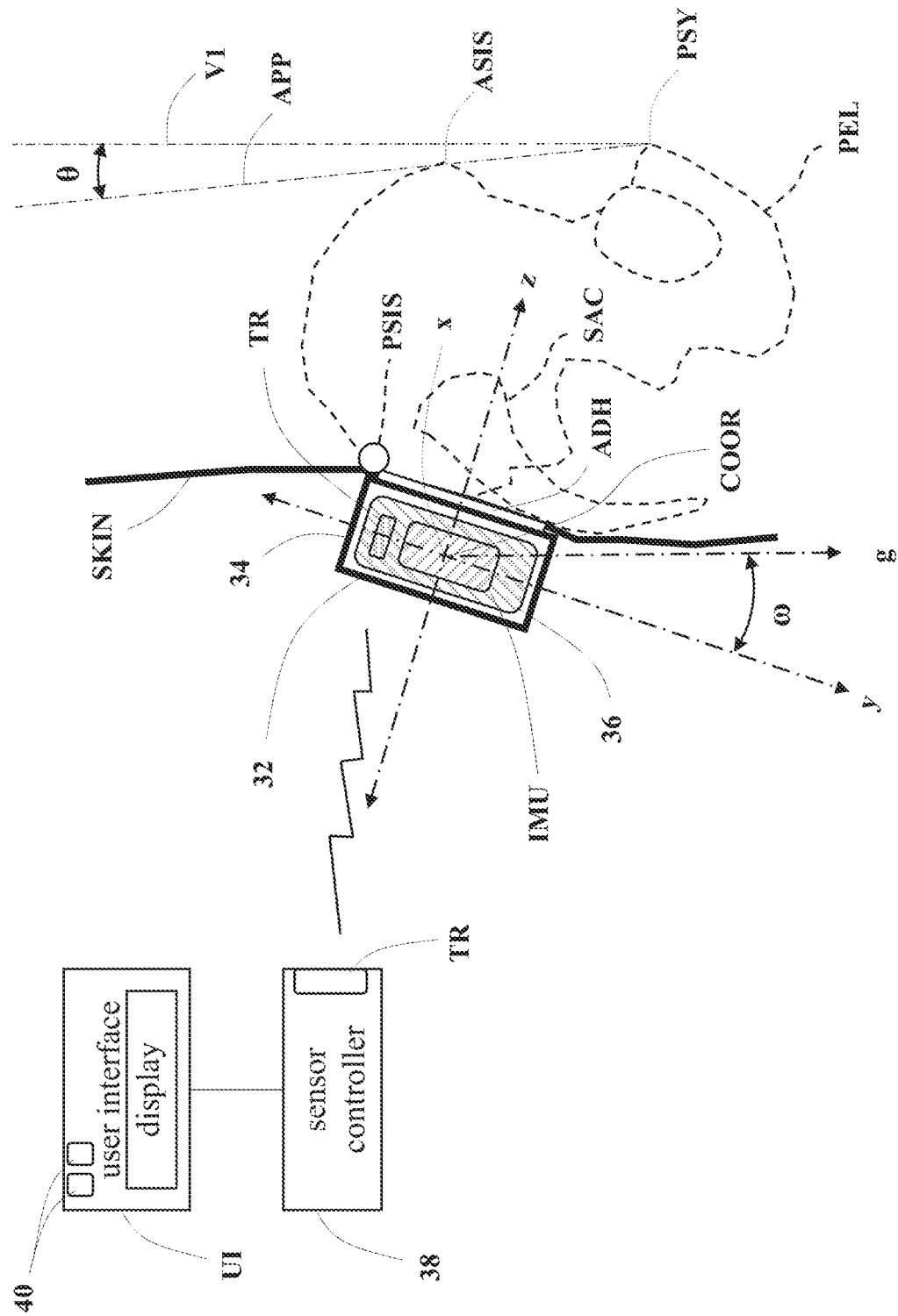
FIG. 1C illustrates a cross-sectional view of a pelvic sensor.

Referring to FIG. 1C, the pelvic sensor 32 includes a sensor body 34 and an inertial measurement unit (IMU) disposed within the sensor body 34. The IMU may include one or more accelerometers, gyroscopes, and magnetometers to measure linear and angular velocities and positions relative to the coordinate reference frame COOR of the pelvic sensor 32 having x, y, z axes. The IMU may be digital or analog. In some versions, the IMU includes one or more 3-axis accelerometers, one or more 3-axis gyroscopes, and/or one or more 3-axis magnetometers, or any suitable combination thereof. In some versions, the IMU is a 9-axis IMU. In some versions, the IMU includes a 3-axis accelerometer and/or a 3-axis gyroscope, but without any magnetometers. The pelvic sensor 32 includes an internal controller 36 connected to the IMU.

As shown in FIG. 1C, the pelvic sensor 32 may measure a sensor tilt angle ω between the y-axis of the coordinate reference frame COOR and a gravity vector (g) to ultimately determine the pelvic tilt angle θ, as described further below. The x, y, z axes of the coordinate reference frame COOR are located to facilitate such measurement. The x-axis may pass horizontally through a center of the sensor body 34, the y-axis may pass vertically through the center of the sensor body 34, and the z-axis may pass perpendicularly to the x and y axes through the center of the sensor body 34. As a result, if the pelvic sensor 32 is oriented on the skin of the patient P such that the x-axis is horizontal, relative to the gravity vector (g), then readings from the IMU, when the patient P is stationary, will show zero or near zero acceleration or force along the x-axis and will show accelerations (due to gravity) along the y-axis and/or z-axis indicative of the tilt of the sensor body 34 in the yz plane. The sensor tilt angle ω can be calculated based on the accelerations measured along the y-axis and the z-axis and their corresponding right-angle relationship (e.g., $\omega=\tan^{-1}(a_{z\text{-}axis}/a_{y\text{-}axis})$). In some versions, placement of the pelvic sensor 32 may require the user to place the pelvic sensor 32 such that acceleration readings along the x-axis when the patient P is stationary are zero or within a predefined tolerance of zero, and if not, the user may be instructed to reattach the pelvic sensor 32. In some versions, the IMU can compensate for non-zero readings along the x-axis to find the sensor tilt angle ω at horizontal.

A sensor controller 38 is configured to obtain the measurements taken by the pelvic sensors 32, 32a. The pelvic sensors 32, 32a are configured to transmit their measurements to the sensor controller 38 through wired and/or wireless connections between the pelvic sensors 32, 32a and the sensor controller 38 (wireless connection shown in FIG. 1C). The sensor controller 38 may be employed to communicate with the pelvic sensors 32, 32a including instructing the pelvic sensors 32, 32a when to take measurements and receiving the measurements from the pelvic sensors 32, 32a through the wired and/or wireless connections. The internal controllers 36 and the sensor controller 38 may have compatible wired and/or wireless communication components, such as one or more transmitters, receivers, or transceivers TR for receiving and transmitting data, including measurements and measurement instructions, via any suitable protocol, including transmitting and receiving data via radio frequency signals, using WiFi, Bluetooth, Zigbee, etc.

The internal controllers 36 and the sensor controller 38 process the instructions and measurements in accordance with the methods described herein. The internal controllers 36 and/or the sensor controller 38 may have one or more processors for processing instructions or for processing algorithms stored in memory to control operation of the pelvic sensors 32, 32a and coordinate measurement via the pelvic sensors 32, 32a. Additionally, or alternatively, the internal controllers 36 and/or the sensor controller 38 may include one or more microcontrollers, microprocessors, field programmable gate arrays, systems on a chip, discrete circuitry, and/or other suitable hardware, software, or firmware that is capable of carrying out the functions described herein. The internal controllers 36 and/or the sensor controller 38 may have, or may be coupled to, any suitable memory needed for carrying out the functions described herein, such as random access memory (RAM), read only memory (ROM), other non-volatile memory, and may be connected to various secondary storage devices, such as external hard drives and the like. Power to the pelvic sensors 32, 32a (and internal controllers 36) and/or the sensor controller 38 may be provided by battery power supplies and/or an external power source. The sensor controller 38 may be embodied in a laptop computer, other computer, or other data processing device. The sensor controller 38 may be embodied in a portable electronic device such as an iWatch®, iPhone®, iPad®, or similar electronic devices.

A user interface UI with display is coupled to the sensor controller 38 to facilitate operation of the sensor controller 38. The user interface UI includes one or more user input devices 40 coupled to the sensor controller 38 to transmit user input signals to the sensor controller 38. The user interface UI also receives output signals from the sensor controller 38 and displays information on the display that may be of interest to the user. The user interface UI may be used to control operation of the pelvic sensors 32, 32a through the sensor controller 38.

The user input devices 40 may include any device capable of being actuated by the user and may be provided on a control panel, touchscreen, or the like. The user input devices 40 may be configured to be actuated in a variety of different ways, including but not limited to, mechanical actuation (hand, foot, finger, etc.), hands-free actuation (voice, foot, etc.), and the like. The user input devices 40 may include buttons, a gesture sensing device for monitoring motion of hands, feet, or other body parts of the user (such as through a camera), a microphone for receiving voice activation commands, a foot pedal, and sensors. Additionally, the buttons/pedals can be physical buttons/pedals or virtually implemented buttons/pedals such as through optical projection or on a touchscreen. The buttons/pedals may also be mechanically connected or drive-by-wire type buttons/pedals where a user applied force actuates a sensor, such as a switch or potentiometer. The user input devices 40 may include a keyboard, mouse, etc. It should be appreciated that any combination of user input devices may also be utilized.

In some versions, still referring to FIG. 1C, the measurements taken by the pelvic sensor 32 are taken with the patient P in various functional positions to yield a sensor-based pelvic tilt angle θ at each position. The positions selected for measurement can include those associated with known causes of dislocation, such as those associated with squatting, picking up an object from a floor, getting out of a chair, pivot and turn motions, and the like. Additionally, or alternatively, the pelvic sensor 32 may continuously measure the pelvic tilt angle θ to provide a plurality of measurements over time as the patient P moves through different functional positions to produce dynamic pelvic tilt data. In this case, the sensor controller 38 may be operable to identify a maximum pelvic tilt angle, a minimum pelvic tilt angle, a difference between the maximum and minimum, or other metrics may be obtained from the dynamic pelvic tilt data. The sensor-based measurements thus produce patient-specific data that shows the user (e.g., the surgeon and/or others using the system 30) how the pelvic tilt angle θ changes for the patient P at the different functional positions or during certain motions. Such patient-specific data can be used to determine suitable placement for the acetabular implant AI to avoid impingement by the stem implant SI that can lead to dislocations and/or excessive wear of the implants AI, SI.

Figure 2:
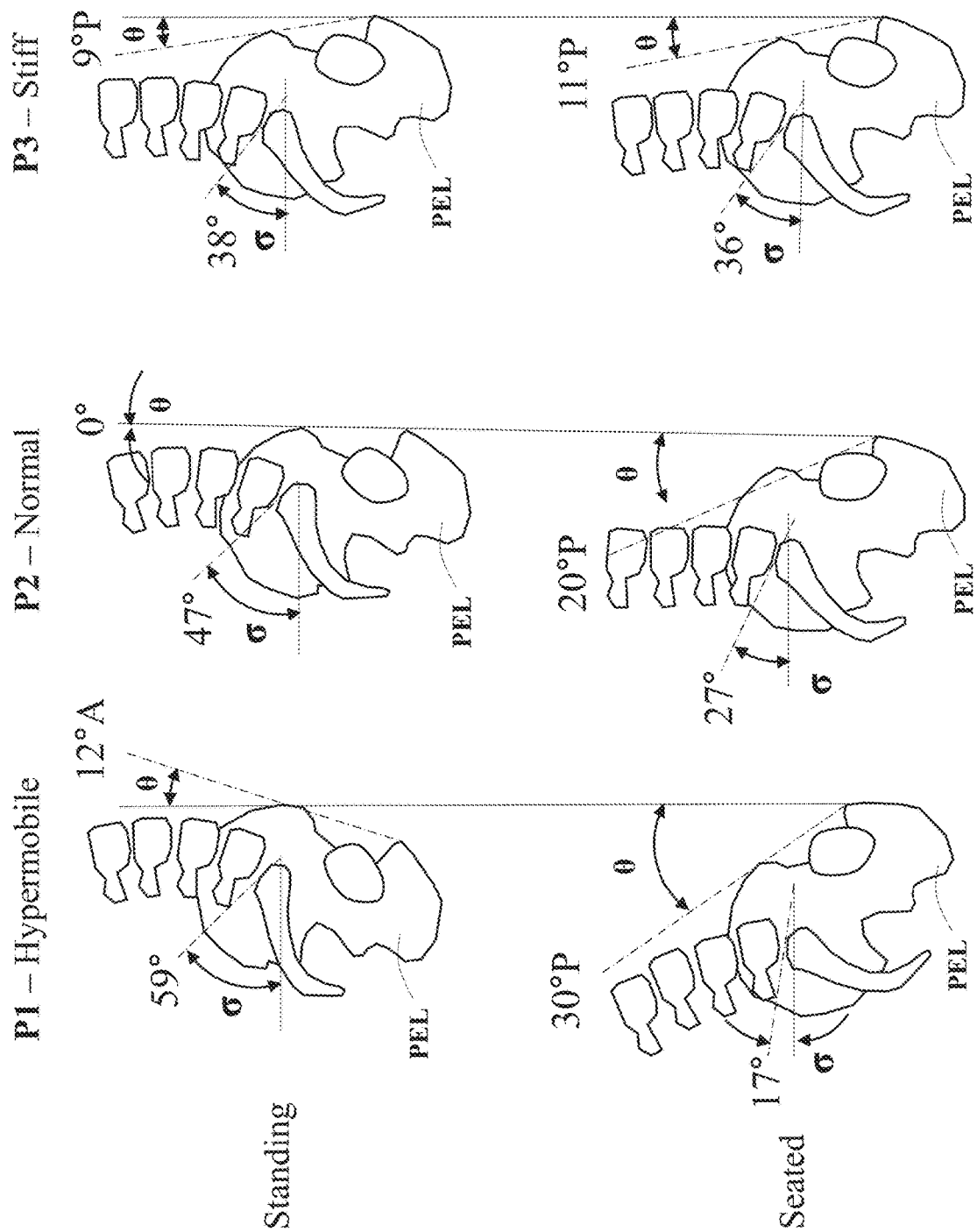
FIG. 2 illustrates various types of spinopelvic mobility and example changes in pelvic tilt and sacral slope for each type between standing and seated positions.

The pelvis PEL naturally flexes forward and backward during certain motions. However, different patients have different spinopelvic mobility, and naturally may have different magnitudes and/or directions of pelvic flexing. Referring to FIG. 2, for example, lateral x-rays for three different patients P1, P2, P3 are shown in standing and seated positions. These patients P1, P2, P3 have different levels of spinopelvic mobility ranging from a stiff spine/pelvis to a hypermobile spine/pelvis and their pelvic tilt angles θ in the standing and seated positions vary. Thus, suitable placement of the acetabular implant AI for these three patients P1, P2, P3 may vary. By tracking pelvic tilt of these patients P1, P2, P3, additional patient-specific data is provided that can assist users in making decisions regarding implant placement by accounting for their individual spinopelvic mobility.

In some cases, as described further below, a user can input the patient-specific data into surgical planning software to plan an inclination angle γ and a version (anteversion) angle λ of the acetabular implant AI for the patient P (see FIG. 3). Effectively, the surgical planning software can show the user how the changes in the pelvic tilt angle θ between the various functional positions can change the position of the acetabular implant AI, e.g., to show how the inclination angle γ and version angle λ of the acetabular implant AI changes. The surgical planning software may also provide range-of-motion (ROM) analysis for each patient to identify potential areas of impingement to the user so that the user can adjust placement of the acetabular implant AI as needed to help reduce the chance for impingement and excessive wear/dislocation.

Figure 3:
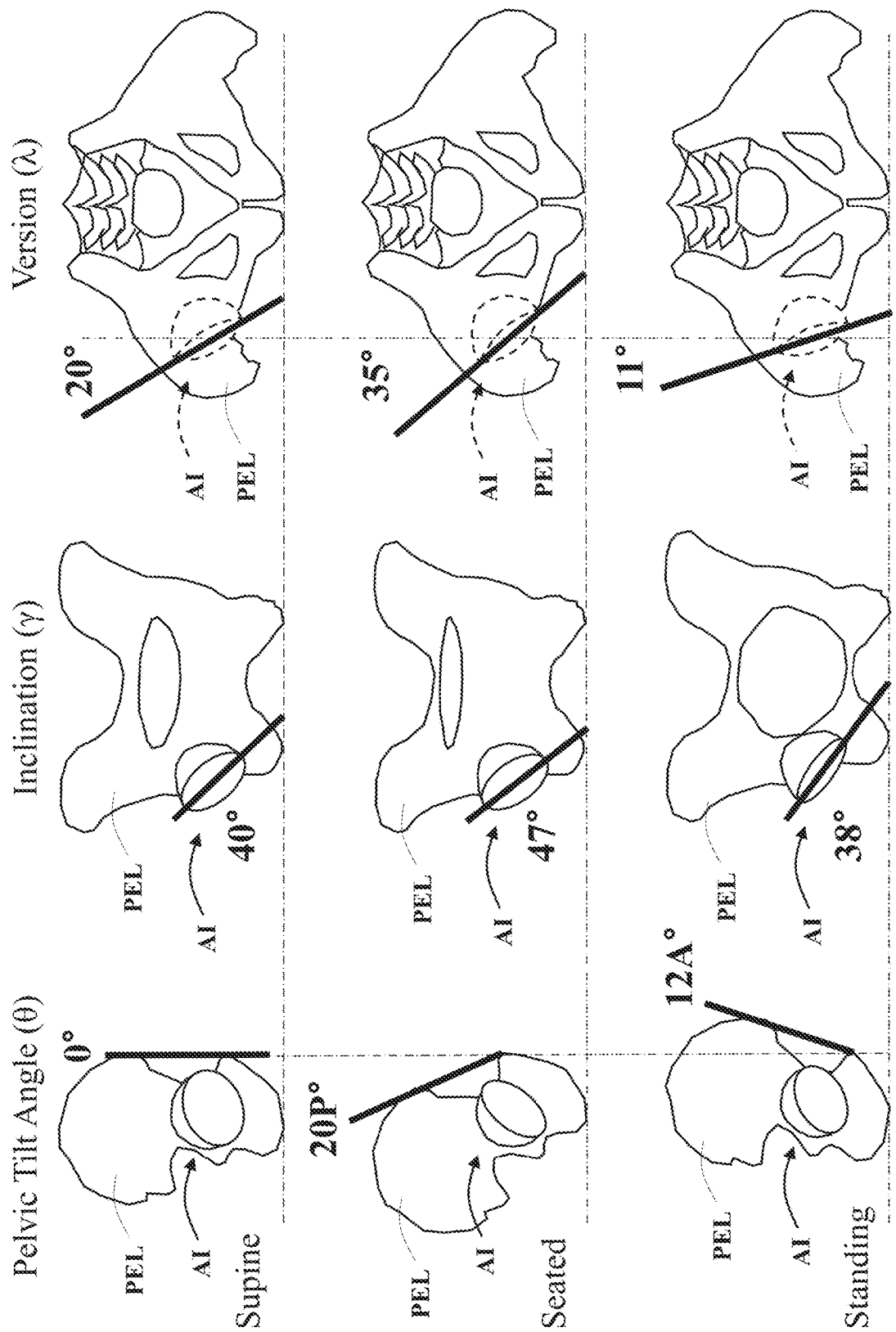
FIG. 3 illustrates how inclination and version of an acetabular implant changes depending on pelvic tilt angle.

FIG. 3 illustrates how the pelvic tilt angle θ can change when the patient P moves to different functional positions, and how the inclination angle γ and version angle λ of the acetabular implant AI change along with changes in the pelvic tilt angle θ. As shown, an example acetabular implant AI has a planned placement at a 40° inclination angle γ and at a 20° version angle λ (anteversion). This placement is based on a pelvic tilt angle θ of the patient P when the patient is in a supine position (shown as 0° in FIG. 3). Often, patients are placed in the supine position during pre-surgical CT imaging used to create three-dimensional (3-D) models of the patient's pelvis and femur for purposes of surgical planning. Accordingly, surgical planning is sometimes based on the pelvic tilt angle θ of the patient P in the supine position. As the patient P moves to a seated position, a standing position, or other functional positions, the pelvic tilt angle θ can change dramatically. For example, as shown in FIG. 3, when sitting, the pelvic tilt angle θ can change from 0° to 20° posterior and, when standing, can change to being 12° anterior. Of course, these are merely examples of changes in pelvic tilt, but each patient will differ in the way their anatomy responds to certain movements, e.g., based on their spinopelvic mobility. As a result, the acetabular implant AI, which is fixed to the pelvis PEL, will also vary widely in its functional placement (e.g., its placement at each functional position) as compared to the planned placement note the changes in the inclination angle γ and the version angle λ of the acetabular implant AI for the standing and seated positions.

The propensity for impingement and associated dislocations may be reduced if placement of the acetabular implant AI is adjusted during surgical planning to account for the variation in movement (or lack thereof) of the patient's pelvis PEL. The following example is illustrative: A patient with normal spinopelvic mobility has a pelvis PEL that tilts posteriorly when sitting. Owing to such posterior tilting, the seated version angle λ of the acetabular implant AI for the patient increases relative to the supine/standing version angle λ. See, for example, FIG. 3 in which the patient's pelvic tilt angle θ changes to 20° posterior when sitting, and the functional version angle λ changes to 35° (anteversion). Accordingly, this patient may be at low risk for dislocation during flexion of the femur F in the seated position or when lifting themselves out of the seated position. On the contrary, referring to FIG. 3A, a patient that has stiff spinopelvic mobility, tends to have little variation in pelvic tilt between supine/standing, and seated positions, and thus little variation in functional version angle λ between these positions. The patient represented in FIG. 3A has no variation in the functional version angle λ between standing and seated positions. If a surgeon initially set a planned version angle λ of 20° (anteversion) for this patient, then both the standing and seated version angle λ would be 20°. Such a patient may be at increased risk for impingement and dislocation during flexion, such as when the patient flexes forward to lift themselves out of the seated position. During such flexed forward motion, the functional version angle λ may even decrease (see, e.g., the decrease to 15° shown in FIG. 3A). As a result, anterior impingement of the stem implant SI could result in posterior dislocation (see arrow in FIG. 3A). To compensate for the lack of flexibility in the patient's pelvis PEL, the surgeon could adjust placement of the acetabular implant AI with a larger planned version angle λ.

By using the system 30, a surgeon can take into account the measurements taken by the pelvic sensor 32 to better understand how the pelvic tilt angle θ for each patient changes between functional positions and/or during certain movements, and fine tune targets for the inclination angle γ and/or version angle λ accordingly to reduce the chances for impingement and implant material wear or dislocation.

Obtaining data on pelvic motion may include obtaining one or more x-ray images, which could include images captured during CT scans, A/P x-ray images, lateral x-ray images, and the like. It is desirable, however, in some cases, to minimize radiation due to imaging, while at the same time obtaining suitable, patient-specific data regarding positions of the pelvis PEL and femur F to determine how best to place the acetabular implant AI. In some versions, a single set of CT images and a single, two-dimensional (2-D) lateral x-ray image may be captured for each patient P. The patient P may be in the supine position when capturing the single set of CT images and the patient P may be in a first functional position (e.g., standing, seated, squatting, bending, etc.) when capturing the single, 2-D lateral x-ray image. The patient is shown standing in FIG. 4. The single set of CT images are used to create the virtual 3-D model or models of the patient's anatomy, including 3-D bone models of the pelvis PEL, femur F, and any other anatomy of interest (such 3-D models could be created in other ways, such as being based on a statistical model and/or selected from a database based on the patient's age, gender, race, prior images, etc). The 2-D lateral x-ray image of the patient P is captured to establish an image-based pelvic tilt angle θ1 for the first functional position (e.g., for the standing position), as shown in FIG. 4, for reasons described below.

In some versions, only a single, 2-D lateral x-ray image is captured (without any CT images) with the patient in the first functional position to establish the image-based pelvic tilt angle θ1. In some versions, a set of CT images is captured with the patient in the first functional position (i.e., a standing CT scan) to create a 3-D model of the patient's anatomy that can be manipulated (e.g., cross-sectioned) to establish the image-based pelvic tilt angle θ1. In some versions, multiple 2-D x-ray images may be simultaneously taken with the patient P in the first functional position to create a 3-D model of the patient's anatomy. For instance, a 2-D A/P x-ray image and a 2-D lateral x-ray image may be taken simultaneously with the patient P in the first functional position to create a 3-D model of the patient's anatomy, such as with the EOS orthopedic imaging system from EOS imaging, SA of Paris, France. In this case, the 2-D lateral x-ray image may be used to establish the image-based pelvic tilt angle θ1 or the 3-D model may be manipulated to determine the image-based pelvic tilt angle θ1.

The sensor controller 38 may be coupled to an image system (e.g., a picture archiving and communications system (PACS)) and/or other system (e.g., a proprietary surgical planning system) such as through a network connection (e.g., Internet or other network)(See FIG. 1). The imaging devices that capture the x-ray images are also coupled to the PACS and/or the proprietary system to store the x-ray images and/or the 3-D models created therefrom in the PACS and/or in the proprietary system. The sensor controller 38 can obtain the one or more x-ray images and/or 3-D models of the patient P by retrieving them from the PACS or from the proprietary system in response to a user request made via the user interface UI. The sensor controller 38 may establish the image-based pelvic tilt angle θ1 by: (i) receiving the image-based pelvic tilt angle θ1 from the PACS or proprietary system if the image-based pelvic tilt angle θ1 is stored along with the one or more x-ray images and/or 3-D models in the PACS or the proprietary system; (ii) measuring the image-based pelvic tilt angle θ1 on the one or more x-ray images or via the 3-D models when retrieved from the PACS or the proprietary system using the user interface UI, such as by the user drawing virtual lines for the anterior pelvic plane (APP) and the vertical line V1 and electronically measuring the pelvic tilt angle θ therebetween; or (iii) receiving the image-based pelvic tilt angle θ1 by virtue of the image-based pelvic tilt angle θ1 being input by a user and stored in the PACS, the proprietary system, the sensor controller 38, or other memory after the image-based pelvic tilt angle θ1 is measured by the user (e.g., electronically or by hand on a hard copy of the one or more images).

Other suitable methods for establishing the image-based pelvic tilt angle θ1 are also contemplated. For instance, a single A/P x-ray image may be captured in the first functional position instead of the single lateral x-ray image. It may be difficult to measure the pelvic tilt directly on the A/P x-ray image, but the A/P x-ray image can be matched up to a 3-D model of the patient's pelvis PEL (such as a 3-D model taken with the patient P in the supine position) to determine the image-based pelvic tilt angle θ1. This can be accomplished by virtually tilting the 3-D model of the pelvis P in the A/P direction while displaying an A/P cross-section of the 3-D model on the display until the A/P x-ray image visually matches the A/P cross-section. The A/P x-ray image could be virtually overlaid onto the A/P cross-section, or vice versa, to determine a suitable match. The A/P cross-sections could also be converted into simulated radiographs to make matching easier. The system 30 or the user then determines how much the 3-D model of the pelvis PEL was tilted to achieve the match thereby identifying the image-based pelvic tilt angle θ1. The image-based pelvic tilt angle θ1 could also be measured on the display using angle measuring software on a portable electronic device (e.g., iPhone®, iPad, or other electronic devices). For example, when a 2-D lateral x-ray image is shown on the display, the user places the portable electronic device up against the display in the same orientation as the anterior pelvic plane (APP). The angle measuring software then outputs an angle value that corresponds to the image-based pelvic tilt angle θ1. In some cases, the CT scan may be performed with the patient in the standing position and the image-based pelvic tilt angle θ1 can be determined based on the CT scan.

Referring to FIG. 4, one or more initial measurements are taken by the pelvic sensor 32 with the patient P in the first functional position (e.g., standing) to establish an initial sensor tilt angle ω1. These initial measurements are taken substantially simultaneously with capturing the one or more images of the patient P and in the same, first functional position. As a result, the initial sensor tilt angle ω1 can be correlated to the image-based pelvic tilt angle θ1. In some versions, the initial sensor tilt angle ω1 is calculated as an angle between the y axis of the pelvic sensor 32 and the gravity vector (g), as previously described (see FIG. 1C).

The sensor controller 38 is configured to correlate the initial sensor tilt angle ω1 to the image-based pelvic tilt angle θ1 by: (i) setting the value of the initial sensor tilt angle ω1 to the value of the image-based pelvic tilt angle θ1; or (ii) zeroing the initial sensor tilt angle ω1 such that subsequent measurements by the pelvic sensor 32 are made relative to the image-based pelvic tilt angle θ1. When the initial sensor tilt angle ω1 is set equal to the value of the image-based pelvic tilt angle θ1, subsequent measurements with the pelvic sensor 32 are of the actual pelvic tilt angle θ. For example, FIG. 4 shows the patient P with the image-based pelvic tilt angle θ1 being 15° anterior and the initial sensor tilt angle being 30°. The sensor tilt angle ω is set/calibrated to 15° such that additional measurements of the sensor tilt angle ω correspond to the pelvic tilt angle θ, e.g., if the sensor tilt angle ω changes to 10°, for example, then the pelvic tilt angle θ is 10° anterior. Note that posterior pelvic tilt angles have a negative (−) value. So, for example, if FIG. 4 shows an initial sensor tilt angle ω1 of +20° and an image-based pelvic tilt angle θ1 of −5° (posterior), then the sensor tilt angle ω is set/calibrated to −5° and the sensor tilt angle ω increases in value (less negative initially) with pelvic tilt in the clockwise direction. When the initial sensor tilt angle ω1 is zeroed, the subsequent measurements taken by the pelvic sensor 32 are still considered to be measurements of the pelvic tilt angle θ, but the values obtained are relative pelvic tilt angles, not actual pelvic tilt angles θ. However, these relative pelvic tilt angles could later be compensated based on the image-based pelvic tilt angle θ1 to obtain the actual pelvic tilt angles θ, if desired.

It should be appreciated that the correlation between the sensor tilt angle ω and the pelvic tilt angle θ may be affected by patients having a high body mass index (BMI). Patients with high BMI may have more soft tissue covering their pelvis PEL such that the pelvis PEL moves beneath the patient's skin relative to the pelvic sensor 32. In these cases, a correction factor may be applied to correct the sensor measurements. For instance, if BMI is above 40, 50, 60, etc. then different correction factors can be added to the sensor measurements, e.g., adding 3°, 4°, 5°, respectively, to the sensor measurements.

Figure 5:
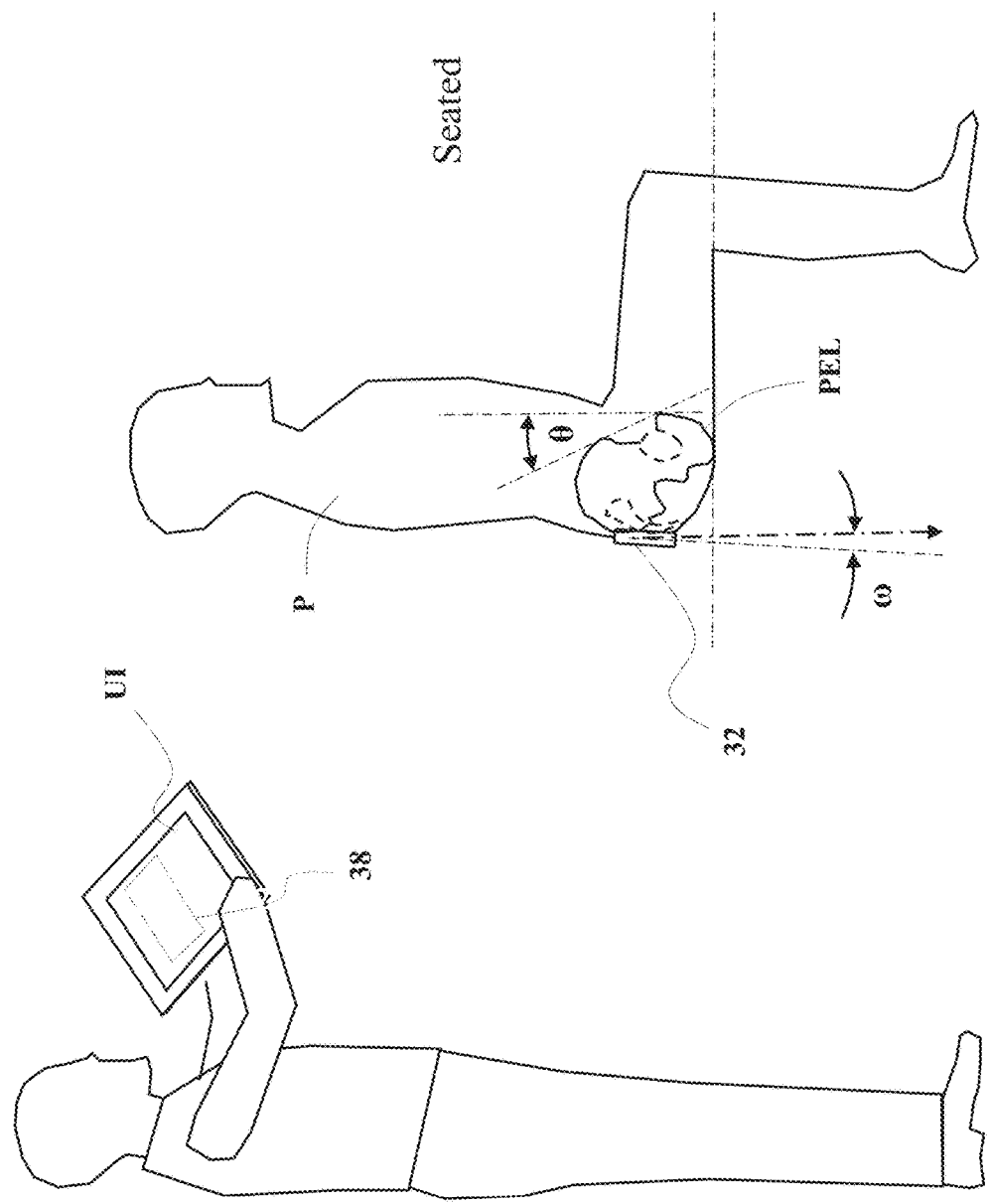
FIG. 5 illustrates the user taking one or more measurements of pelvic tilt with the sensor while the patient is in a seated position.
Figure 6:
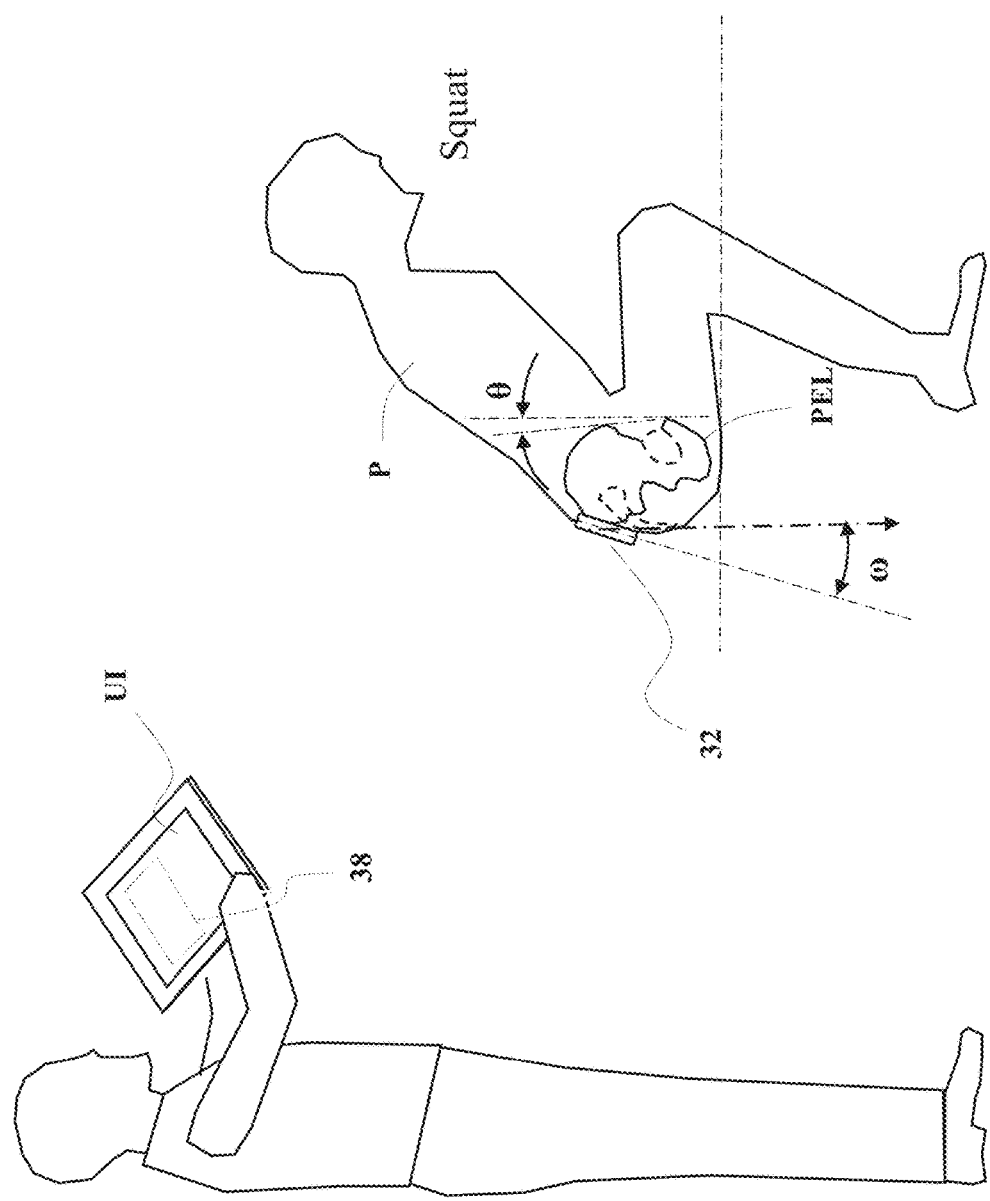
FIG. 6 illustrates the user taking one or more measurements of pelvic tilt with the sensor while the patient is in a squat position.
Figure 7:
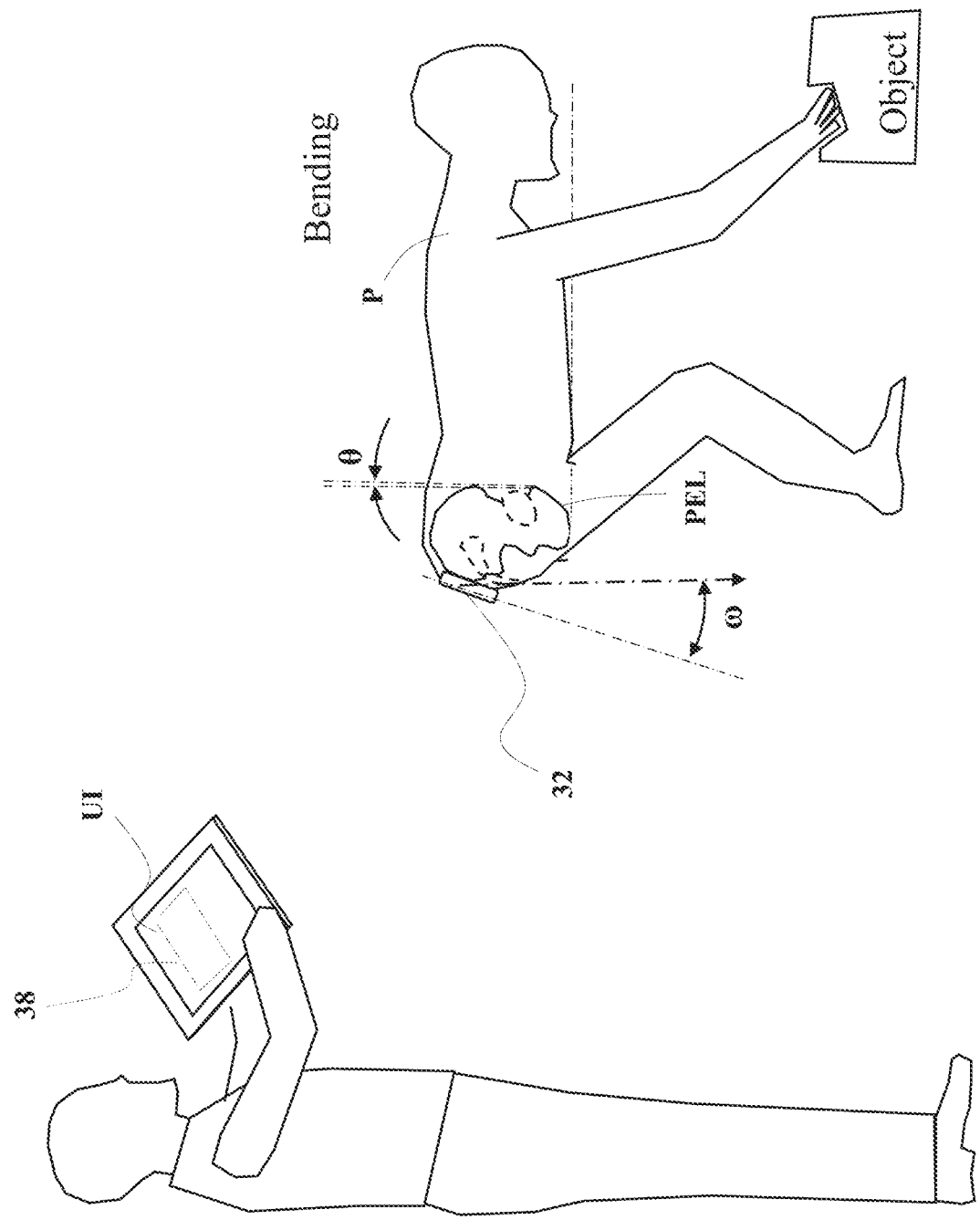
FIG. 7 illustrates the user taking one or more measurements of pelvic tilt with the sensor while the patient is in a bending position and picking up an object from a floor.

Once the correlation between the initial sensor tilt angle ω 1 and the image-based pelvic tilt angle θ1 is made, additional measurements of the pelvic tilt angle θ can be made using the sensor 32 in an image-free mode, i.e., without any further imaging of the patient P being required. Thus, patient-specific data can be provided by the system 30 while limiting radiation exposure due to radiographic imaging. Additional sensor-based measurements are shown being taken in FIGS. 5 through 7, in which the patient P moves to additional functional positions, different than the first functional position, including a seated position, a squat position, and a bending position picking up an object from a floor. Other functional positions and movements are also contemplated in which the pelvic sensor 32 takes additional measurements to produce the patient-specific data based on pelvic tilt that can be used to plan placement of the acetabular implant AI.

In some versions, the additional sensor-based measurements may indicate that further images should be taken of the patient P such as in cases involving complex spinopelvic movement. For example, the sensor controller 38 may be operable to determine whether the patient P requires one or more additional x-ray images to be taken based on the additional sensor-based measurements, such as when the sensor controller 38 determines that the pelvic tilt angle θ has changed more than a predetermined threshold between two functional positions or if a graph of the pelvic tilt angle θ during certain motions shows an unusual pattern. For example, the sensor controller 38 may monitor changes in the pelvic tilt angle θ between functional positions and indicate to the user (e.g., on the display with text, graphics, etc.) when the pelvic tilt angle θ changes more than a threshold amount (e.g., more than 10°, 20°, or 30° between positions). The sensor controller 38 may also monitor for changes of less than or equal to a threshold amount to identify patients with stiff spinopelvic mobility. For example, the sensor controller 38 may indicate to the user (e.g., on the display with text, graphics, etc.) when the pelvic tilt angle θ changes less than 10°, 5°, 1°, etc. between positions).

The image-based and sensor-based measurements may be associated with the patient P by associating the values of the measurements with the patient P via a unique patient identification (ID), e.g., patient name, social security number, account number, etc. The measurements may be stored in memory (e.g., in a look-up table) associated with the unique patient identification (ID). The measurements may also indicate the functional position associated with each measurement, such as by a prefix or suffix attached to each measurement or some other form of identifier. The measurements and associated positions or motions and unique patient identification (ID) may also be stored in a database, or in any suitable digital structure for later retrieval.

FIGS. 8 through 18 illustrate a planning interface PI with various screens for interfacing with surgical planning software. The surgical planning software operates on a planning controller 50 (see FIG. 1). The planning controller 50 may be embodied in a laptop computer, or other suitable computer, and/or may be configured much like the sensor controller 38, as previously described, or may be embodied in the sensor controller 38 (e.g., the sensor controller 38 and the planning controller 50 are integrated). In the version shown, the planning interface PI comprises a touchscreen with display that is connected to the planning controller 50. Other forms of user interface, like those previously mentioned, may also be used. The measurements taken by the pelvic sensor 32 can be input into the planning controller 50 for use by the surgical planning software. The planning controller 50 may obtain the measurements by: (i) manually entering the values of the measurements into the planning controller 50 via the planning interface PI; (ii) transferring the values of the measurements to the planning controller 50 via the network in response to a request from a user of the surgical planning software (e.g., via the planning interface PI); (iii) retrieving the values of the measurements from the sensor controller 38, by wire and/or wirelessly, in response to a request from the user of the surgical planning software (e.g., the planning controller 50 may be connected to the sensor controller 38 via the network); (iv) accessing the values of the measurements stored in the sensor controller 38 when the surgical planning software runs on the sensor controller 38; and/or (v) transmitting, by wire and/or wirelessly, the values of the measurements directly to the planning controller 50 from the pelvic sensor 32.

The planning controller 50 may comprise any suitable configuration of input, output, and processing devices suitable for carrying out the functions and methods described herein. The planning controller 50 may comprise one or more microcontrollers, field programmable gate arrays, systems on a chip, discrete circuitry, sensors, displays, user interfaces, indicators, and/or other suitable hardware, software, or firmware that is capable of carrying out the functions described herein. The sensor controller 38 and the planning controller 50 may collectively be considered part of a system controller 52. The system controller 52 may comprise the sensor controller 38, the planning controller 50, one or more other controllers, or any combination thereof, or may comprise only one of these controllers. These controllers may communicate via a wired bus or communication network, via wireless communication, or otherwise. The system controller 52 may also be referred to as a control system.

Figure 8:
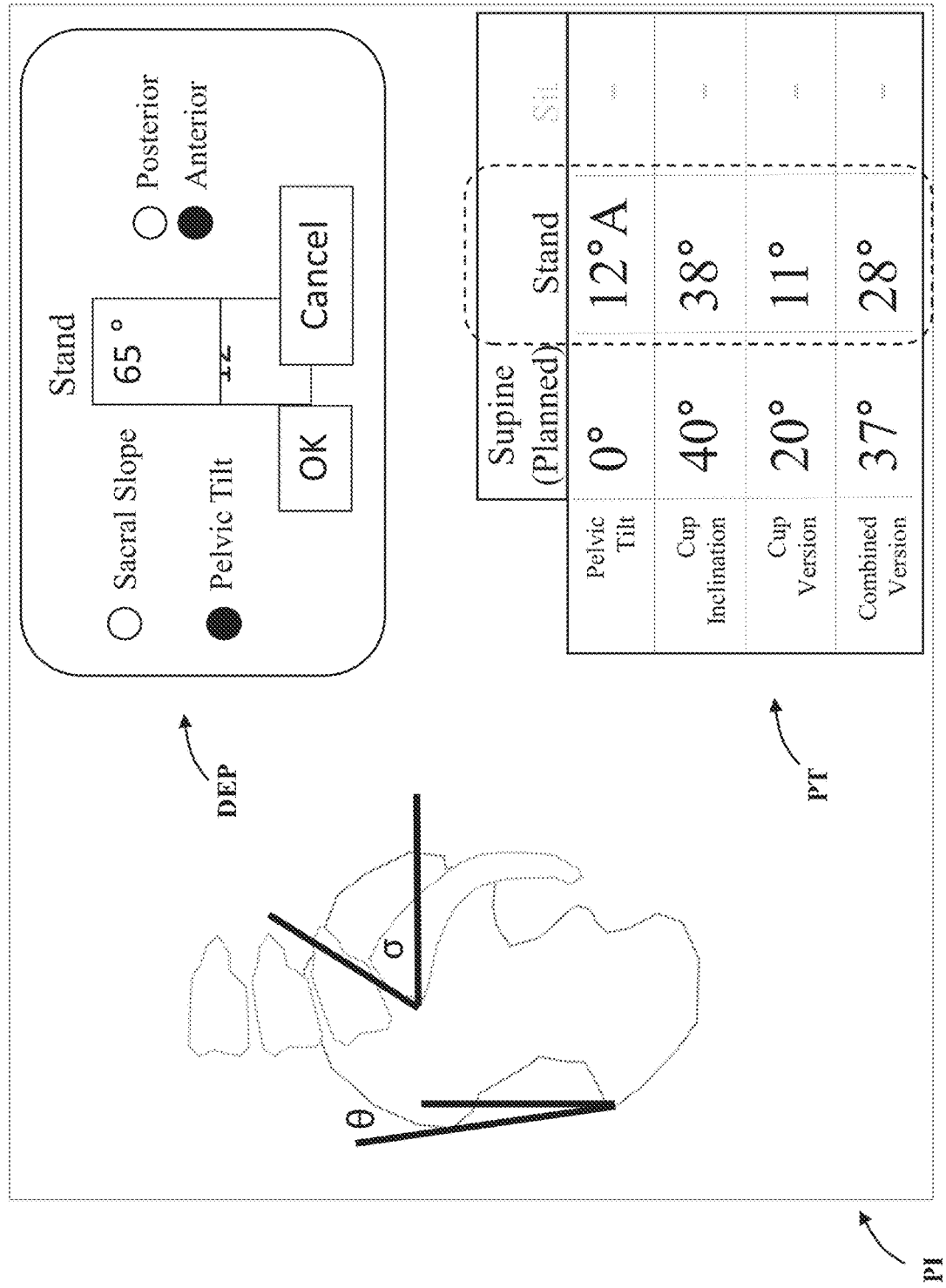
FIG. 8 shows a planning interface with a screen to enter a pelvic tilt angle or sacral slope angle for the patient in standing and seated positions.

In FIG. 8, the planning interface PI shows that the surgeon has already planned a placement for the acetabular implant AI (referred to as "Cup" on the planning interface PI), including a planned inclination angle γ of 40° and a planned version angle λ of 20° based on the patient P being in the supine position, e.g., because the patient P was in the supine position during CT imaging, which was used to create the virtual 3-D models of the patient's anatomy used in the surgical planning software. FIG. 8 also shows how the surgeon can begin to additionally consider the patient-specific data based on pelvic tilt that is provided by the system 30. More specifically, the planning interface PI presents a screen for the user to manually enter pelvic tilt angles θ of the patient P at various functional positions. The version shown in FIG. 8 illustrates the ability to enter pelvic tilt angles θ for the standing ("Stand") and seated ("Sit") positions, but pelvic tilt angles could be entered for other positions as well.

A data entry portion DEP of the screen prompts the user to manually enter the pelvic tilt angles θ for the patient P. Alternatively, the user may enter sacral slope angles σ for the patient P. The sacral slope angle σ can be used as a substitute for the pelvic tilt angle θ when a relationship has been established between the sacral slope angle σ and the pelvic tilt angle θ. This relationship may be established by identifying, in the surgical planning software, anatomical landmarks of the patient P associated with sacral slope and pelvic tilt. This allows the surgical planning software to correlate sacral slope to pelvic tilt. This relationship could also be manually established, e.g., by measuring on the CT images. This relationship can be useful when it is difficult to discern the pelvic tilt angle θ in the 2-D lateral x-ray image. The measurements of sacral slope angle σ are also considered to be measurements of the pelvic tilt angle θ owing to changes in sacral slope having a 1:1 relationship to changes in pelvic tilt (see, e.g., FIG. 2). In other words, once an initial relationship between the sacral slope angle σ and the pelvic tilt angle θ is established, then measurements of sacral slope angle σ can be used to determine measurements of pelvic tilt angle θ.

The screen in FIG. 8 shows that the user has the option, in the data entry portion DEP, of selecting whether the pelvic tilt angle θ is posterior or anterior, and then selecting "OK" once the pelvic tilt angle θ is entered (such as via the touchscreen, keyboard, mouse, or other user input device). Once entered, a pelvic tilt table PT is updated on the display. As shown, the pelvic tilt angle θ for the standing position was entered as 12° anterior. The pelvic tilt table PT then automatically populates values associated with the pelvic tilt, including automatically changing the inclination angle γ and the version angle λ of the acetabular implant AI to correspond to the change in pelvic tilt (recall FIG. 3). The surgical planning software has spatially associated a virtual 3-D model of the acetabular implant AI with a virtual 3-D model of the patient's pelvis PEL. Accordingly, the surgical planning software is able to determine, via computer modeling techniques, how the acetabular implant AI will move in response to changes in the pelvic tilt angle θ since the virtual 3-D model of the acetabular implant AI and the virtual 3-D model of the patient's pelvis PEL are effectively fixed together to act as a single rigid body. As shown in FIG. 8, the value of the pelvic tilt angle θ for the seated position ("Sit") still needs to be entered. If the user selects the column associated with the seated position, such as by touching the word "Sit", then the data entry portion DEP will prompt the user to enter the pelvic tilt angle θ for the seated position as well.

Figure 9:
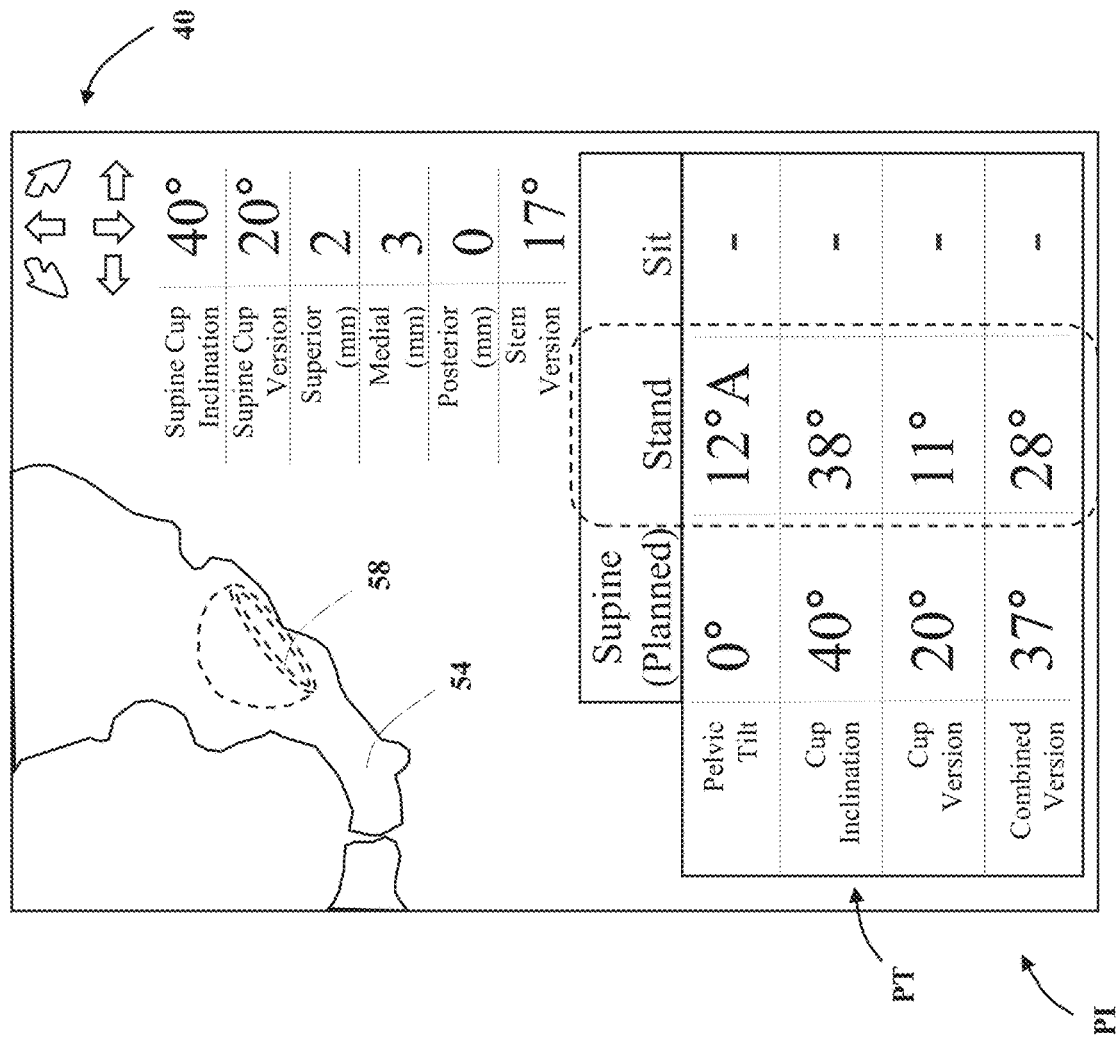
FIG. 9 shows the planning interface with a screen to adjust implant positioning for the patient.

FIG. 9 shows another screen on the planning interface PI. With this screen, the planning interface PI displays values for the planned inclination angle γ and the planned version angle λ of the acetabular implant AI, along with planned positioning for the acetabular implant AI, including values of superior, medial, and posterior placement (in millimeters) (which may be relative to an initial anatomically-centered position). These values are adjustable by the surgeon via user input devices 40 (see arrows) to change positioning of the acetabular implant AI relative to the pelvis PEL to thereby allow the user to refine the placement of the acetabular implant AI based on the patient-specific data associated with pelvic tilt. The values can be changed by selecting the current values and then adjusting them. The stem version is also capable of being input and adjusted by the user on this screen. The pelvic tilt table PT is also shown on this screen and is updated in the event the user alters the positioning of the acetabular implant AI. Through this screen, the user is also able to access the data entry portion DEP to update the pelvic tilt angles θ by selecting one of the pelvic tilt angles θ to be updated.

Figure 10:
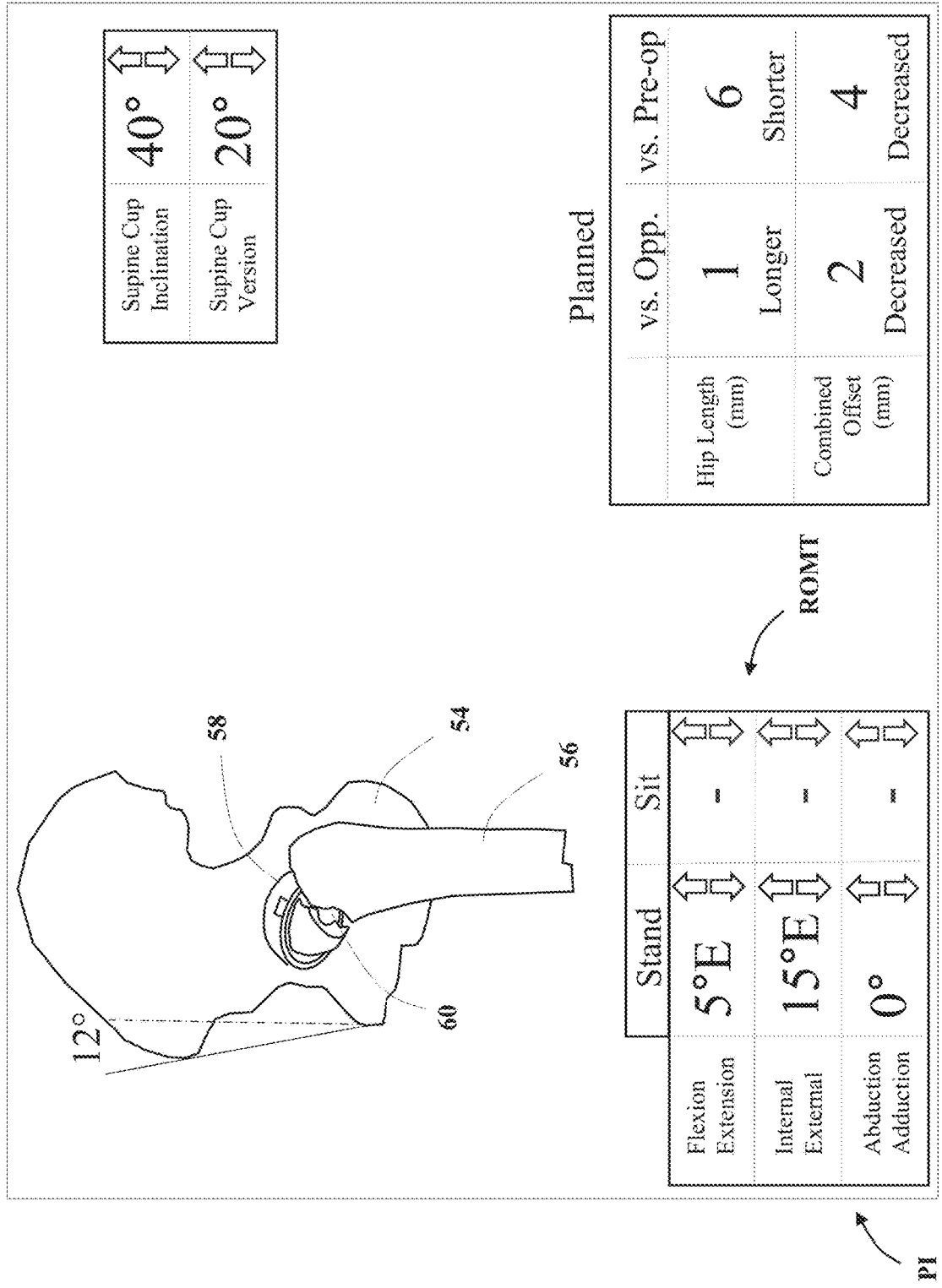
FIGS. 10-12 show the planning interface with screens to analyze the patient's range-of-motion based on current implant positioning and entered pelvic tilt angle for the standing position, with the pelvis, femur, and implants visually represented in different views.
Figure 11:
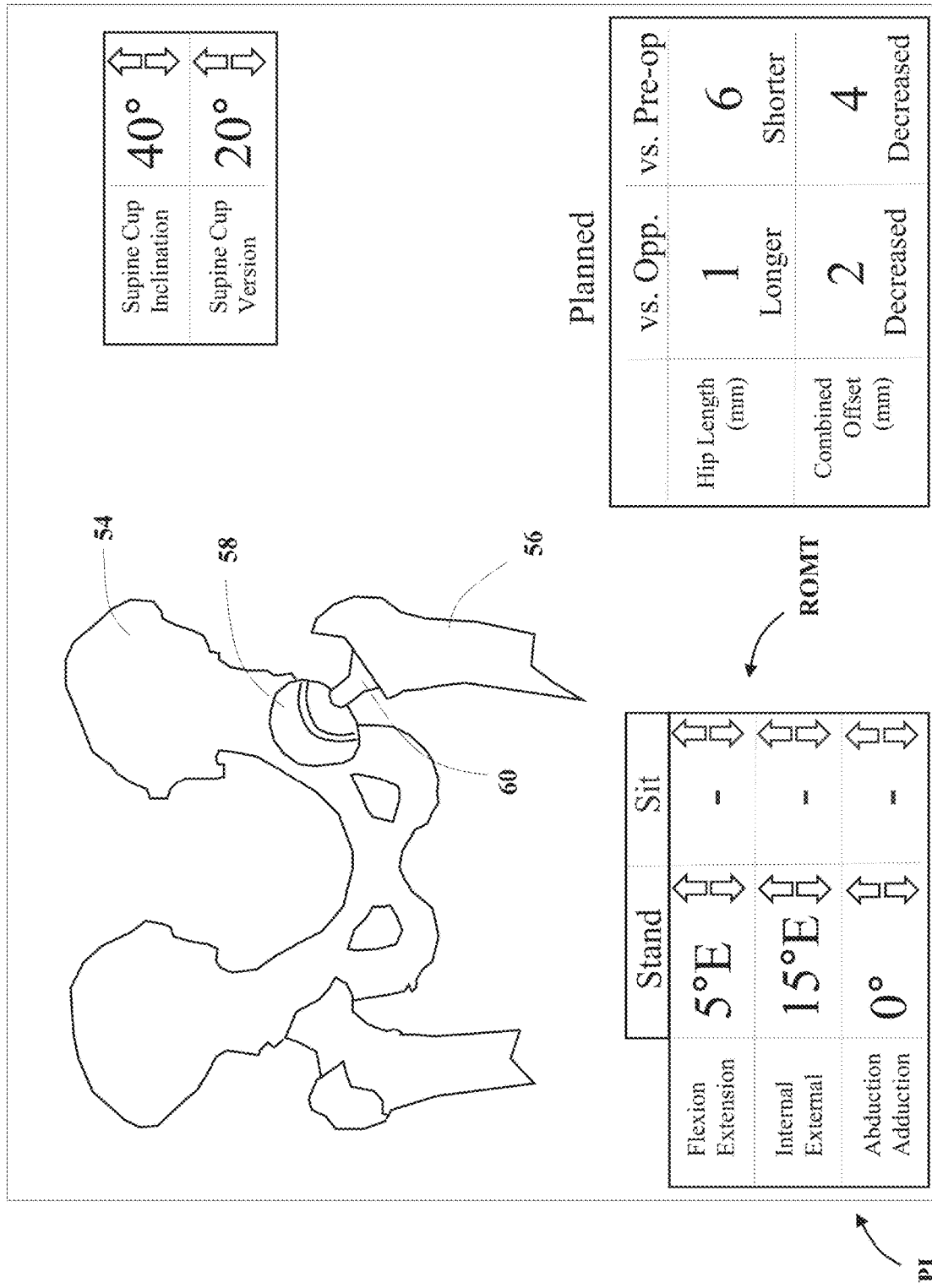
Figure 12:
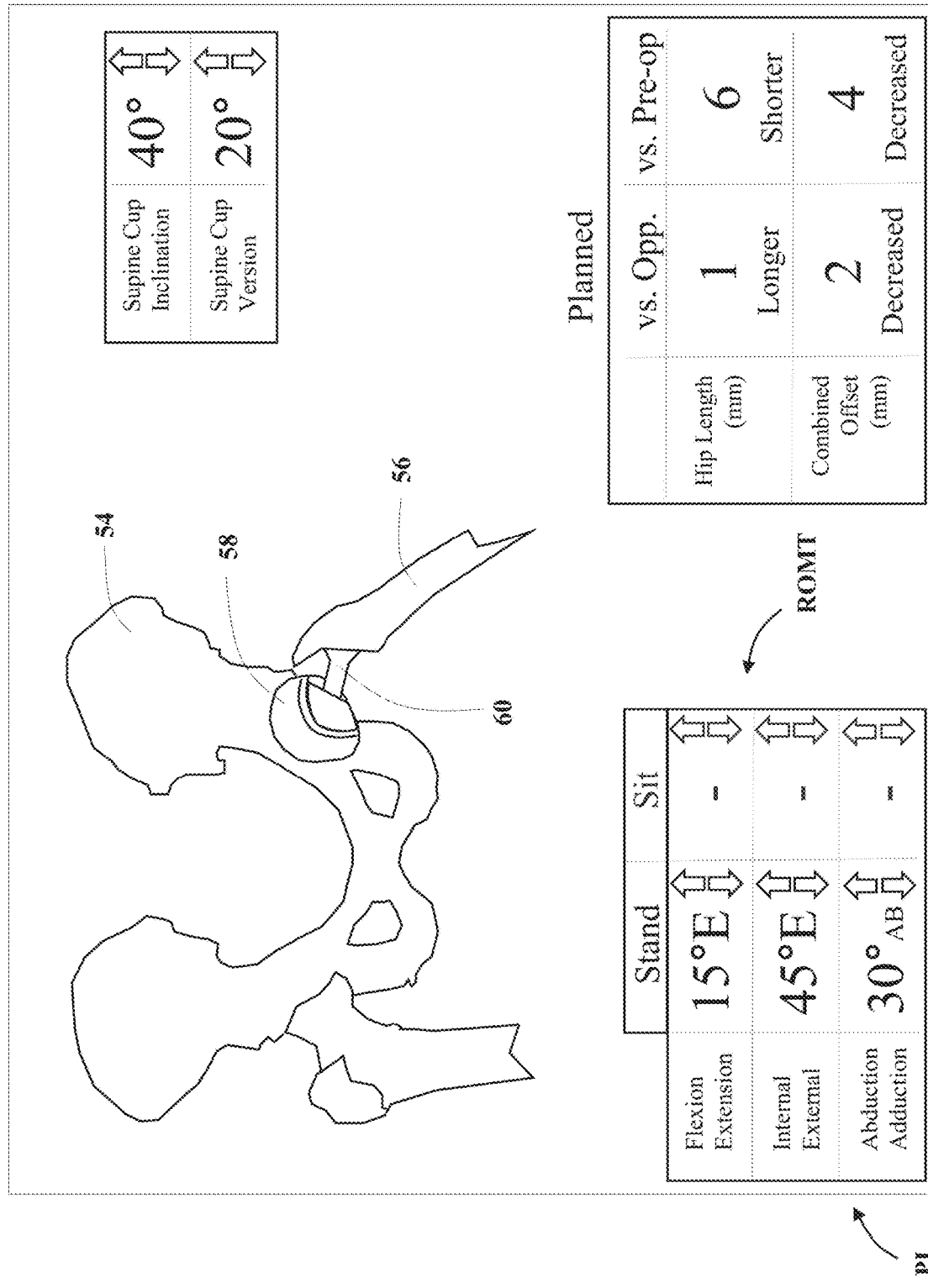
Figure 13:
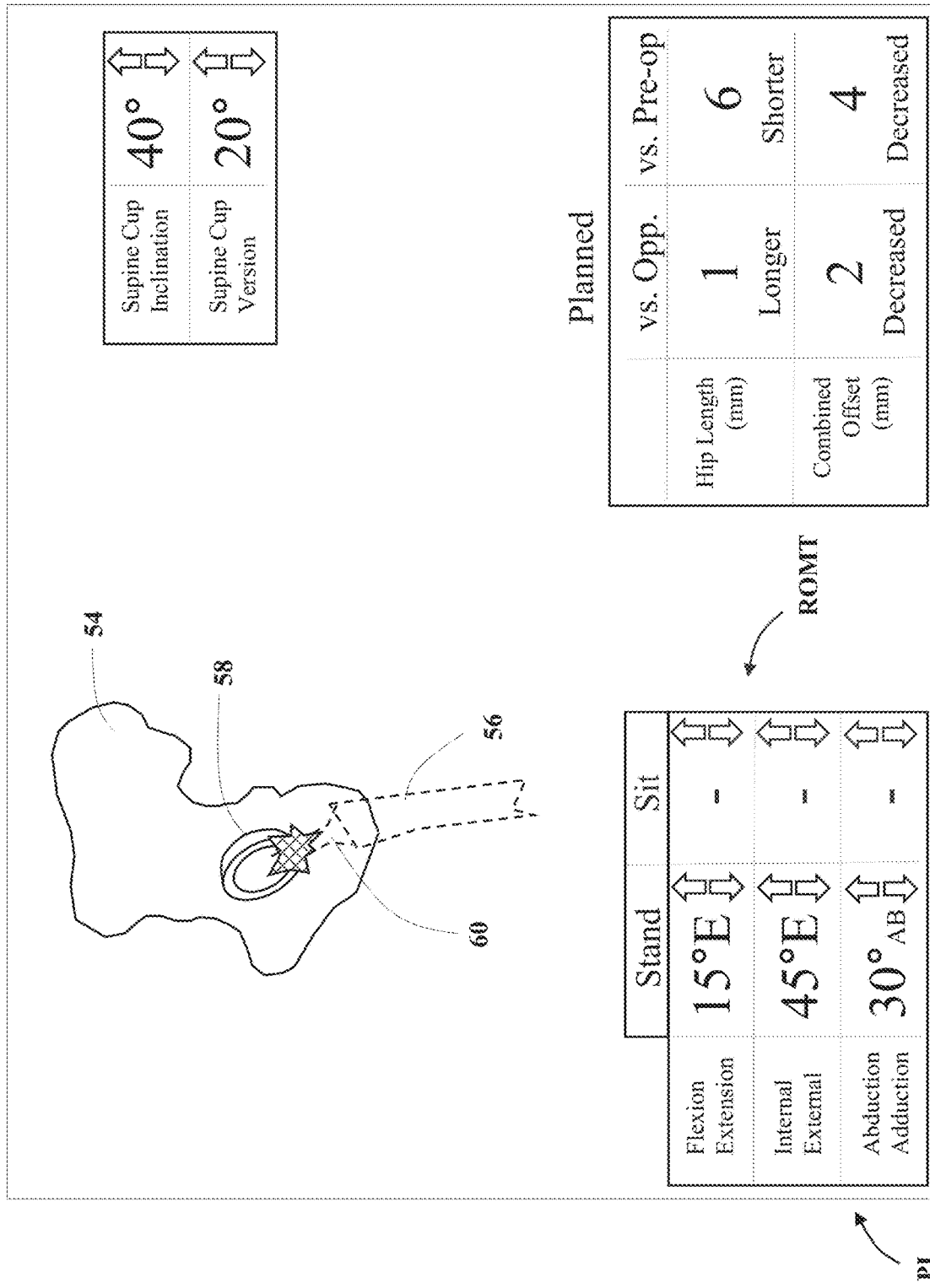
FIG. 13 shows the planning interface with a screen that illustrates impingement that occurs when the patient's anatomy is adjusted as shown in FIG. 12.

FIGS. 10 through 12 illustrate use of a range-of-motion (ROM) module of the surgical navigation software. For example, in FIG. 10, the planning interface PI provides a screen displaying a range-of-motion input table ROMT in which the user can adjust variables associated with the patient's ROM. These variables include angles of flexion/extension, internal/external rotation, and abduction or adduction. These variables can be adjusted for each of the various functional positions for which pelvic tilt angles θ are established in the pelvic tilt table PT (e.g., for the standing position and the seated position in the example shown). FIG. 10 shows the user being allowed to input different values for the various ROM variables to evaluate the patient's range-of-motion in the standing position (seated position is separately evaluated). This screen also shows the planned inclination angle γ and the planned version angle λ of the acetabular implant AI, along with planned leg lengths and offsets (in millimeters).

The planning controller 50 is configured to generate, for display, visual representations 54, 56 of the virtual 3-D models of the pelvis PEL and the femur F and visual representations 58, 60 of the virtual 3-D models of the implants AI, SI. This allows the user (e.g., the surgeon) to visualize on the display how the stem implant SI and the acetabular implant AI are positioned relative to one another based on the ROM inputs from the user. In FIG. 10, the user has entered 5° extension, 15° external rotation, and 0° abduction/adduction. The visual representations 54, 56 of the pelvis PEL and the femur F, and the visual representations 58, 60 of the implants AI, SI are shown in this position on the display and with the pelvic tilt angle θ being 12° anterior (refer back to FIG. 9 for the pelvic tilt angle θ entered for the standing position). In FIG. 10, the patient's anatomy and the implants AI, SI are visually represented in a side view. FIG. 11 shows the same positioning, but in a front view.

FIG. 12 illustrates values that were input for the ROM variables to further evaluate range-of-motion of the patient P in the standing position. In FIG. 12, the user has entered 15° extension, 45° external rotation, and 30° abduction. As shown, the visual representations 54, 56 of the pelvis PEL and the femur F, and the visual representations 58, 60 for the implants AI, SI are moved accordingly on the display (compare FIGS. 11 and 12). In the position of FIG. 12, there is impingement between the implants AI, SI. The surgical planning software may be configured to identify such impingements (e.g., via collision checking algorithms, for example), and display a visual representation of such impingements. Such a visual representation of impingement can be seen in FIG. 13 in which the representation 56 of the femur F and the representation 60 of the stem implant SI have largely been removed or made transparent to illustrate where the impingement occurs via changes in color (e.g., from white or green to red), a starburst graphic, and/or other form of visual indicator. Impingements that may be detected may be implant-to-bone, implant-to-implant, or bone-to-bone impingements.

Figure 14:
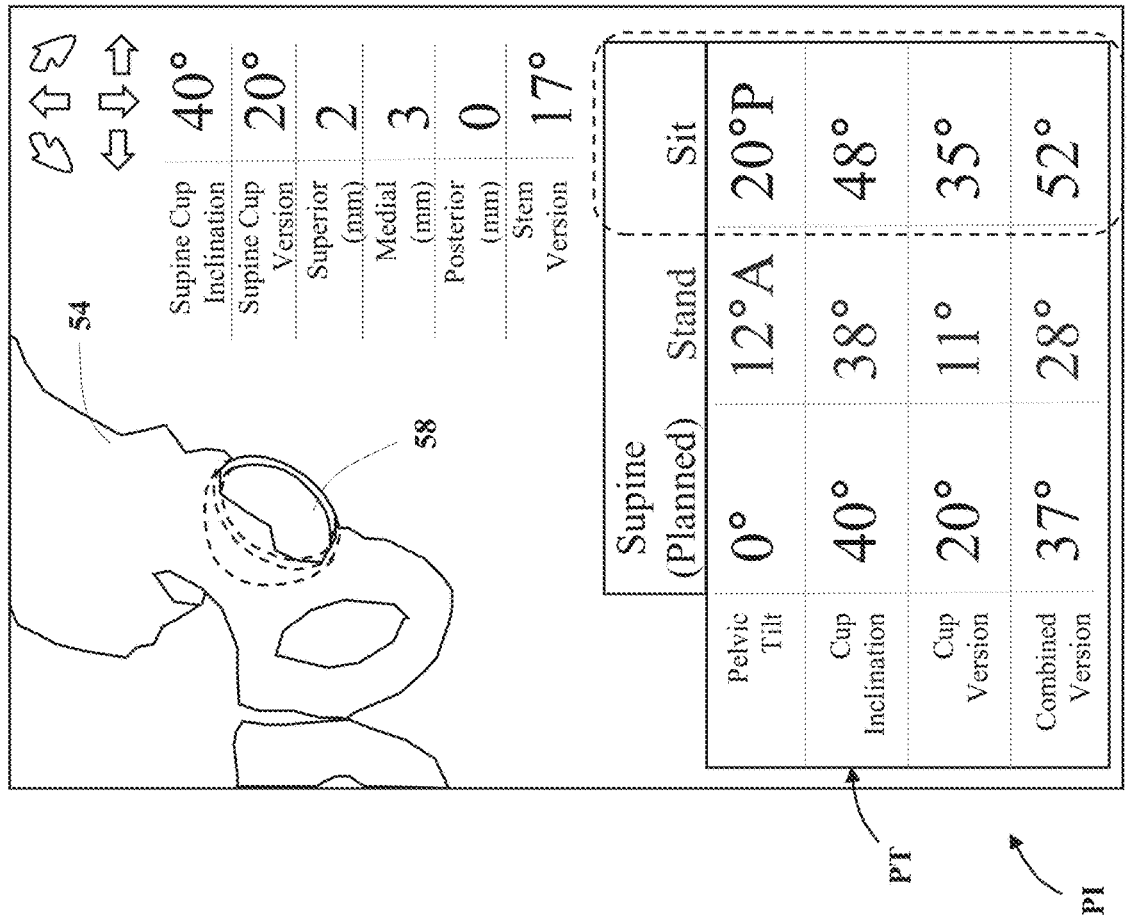
FIG. 14 shows the planning interface with a screen to adjust implant positioning for the patient.
Figure 15:
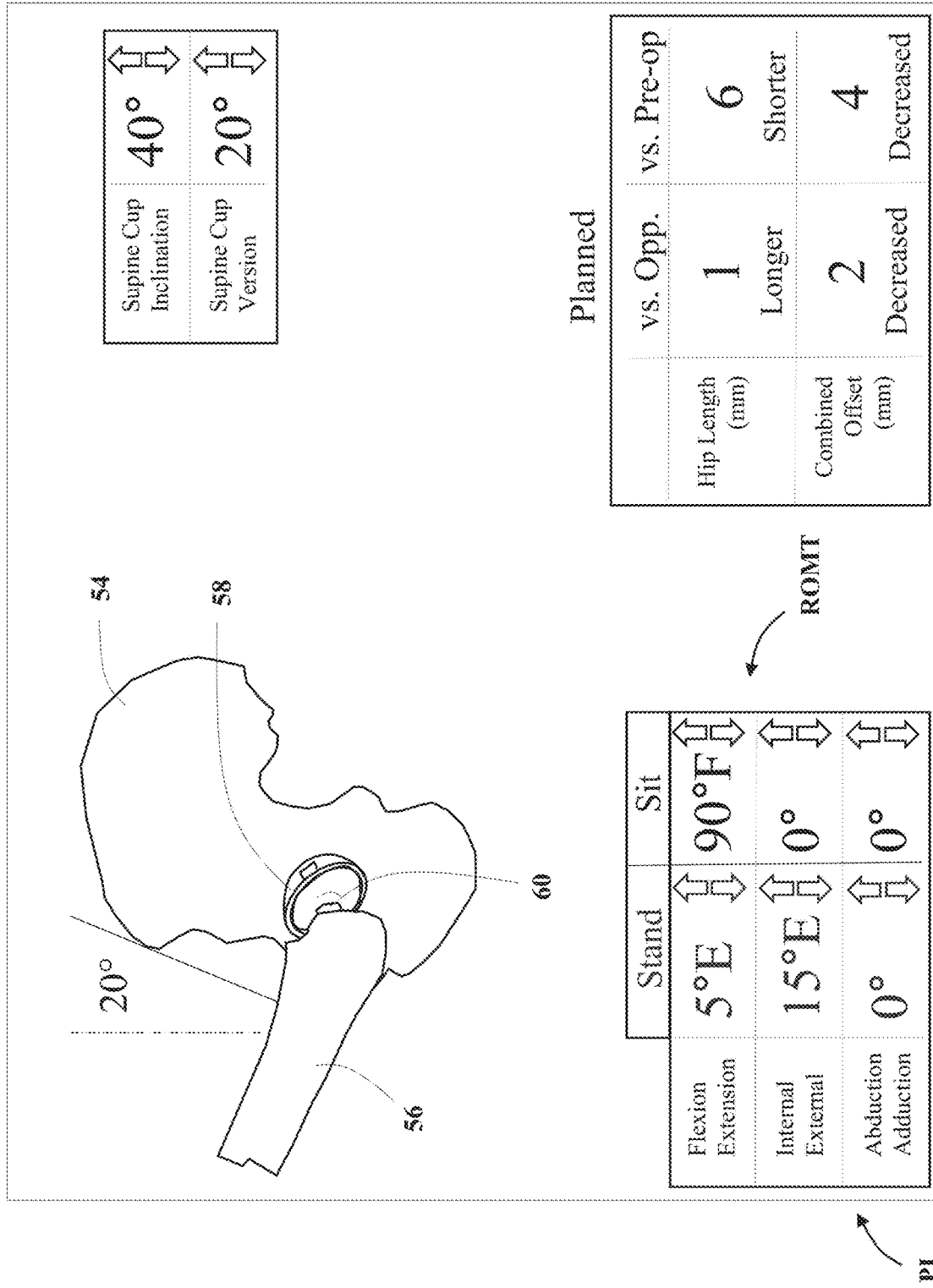
FIG. 15 shows the planning interface with a screen to analyze the patient's range of motion based on the current implant positioning and the entered pelvic tilt angle for the seated position.

FIG. 14 shows the same screen as FIG. 9, but the pelvic tilt table PT has been updated to include a pelvic tilt angle θ for the seated position and associated values for the inclination angle γ and the version angle λ to enable ROM analysis for the seated position, as shown in FIG. 15. FIGS. 14 and 15 represent, for example, a pelvis PEL of a normal patient, e.g., without a stiff spine due to osteoarthritis or spinal fusion, in which pelvic tilt of about 20° posterior when sitting is normal but could be smaller or larger.

Figure 16:
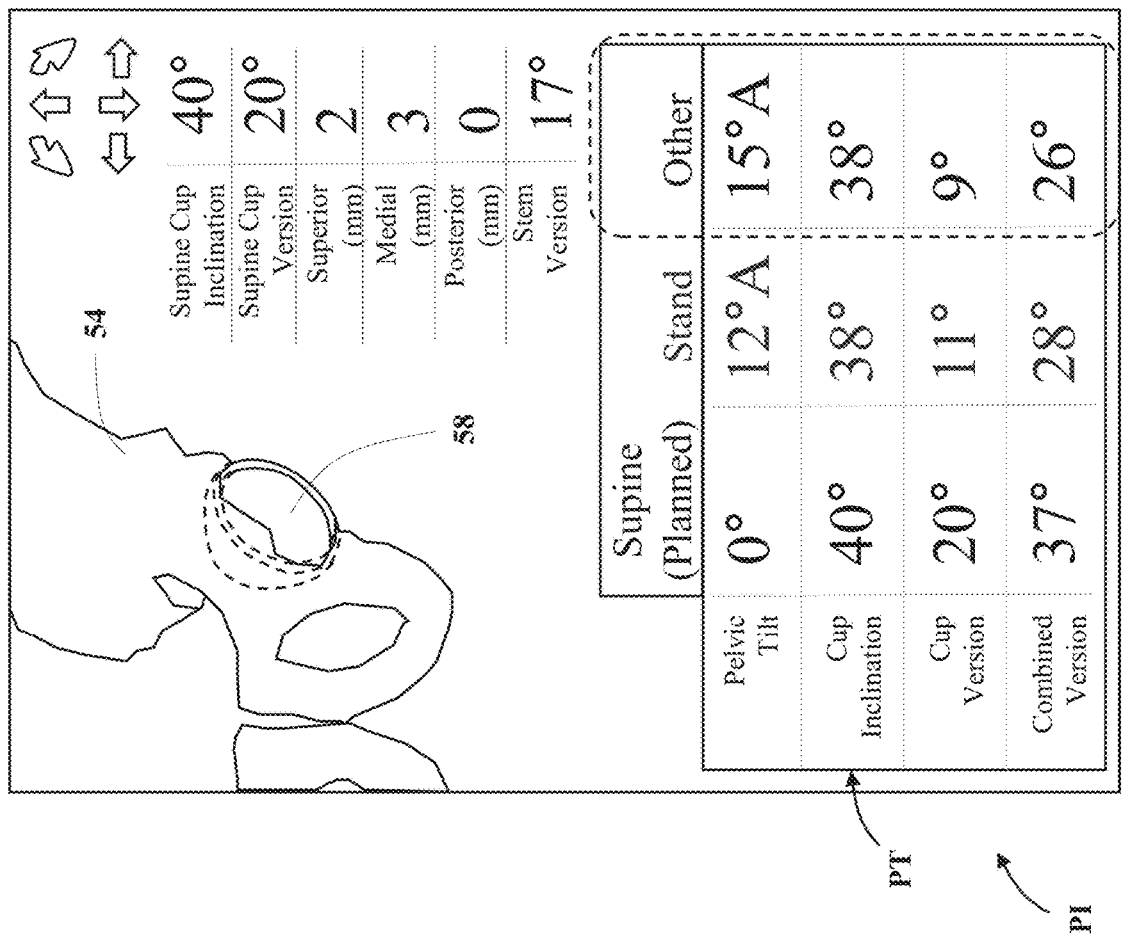
FIG. 16 shows the planning interface with a screen to adjust implant positioning for the patient.
Figure 17:
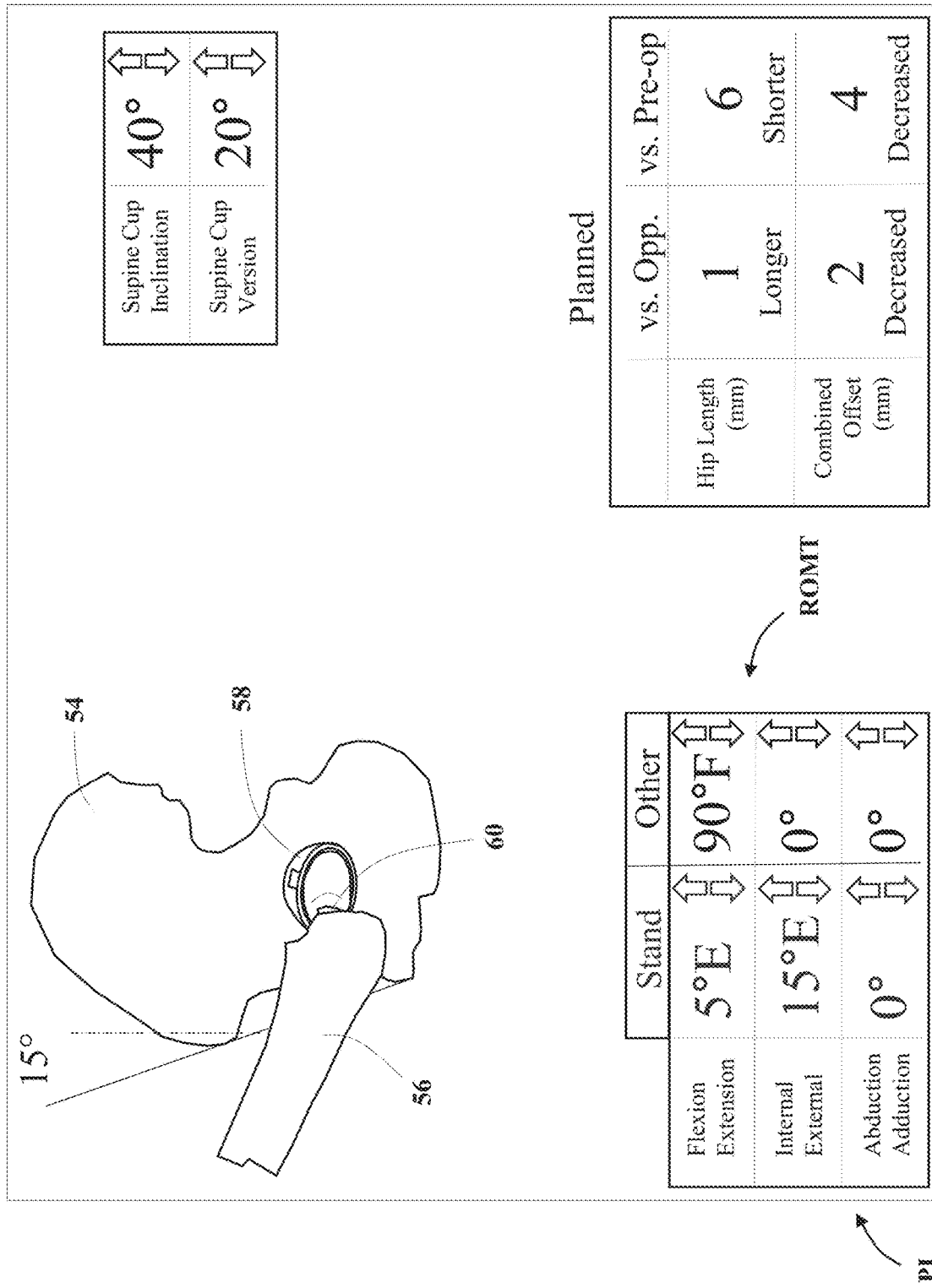
FIG. 17 shows the planning interface with a screen to analyze the patient's range-of-motion based on the current implant positioning and the entered pelvic tilt angle for another position.
Figure 18:
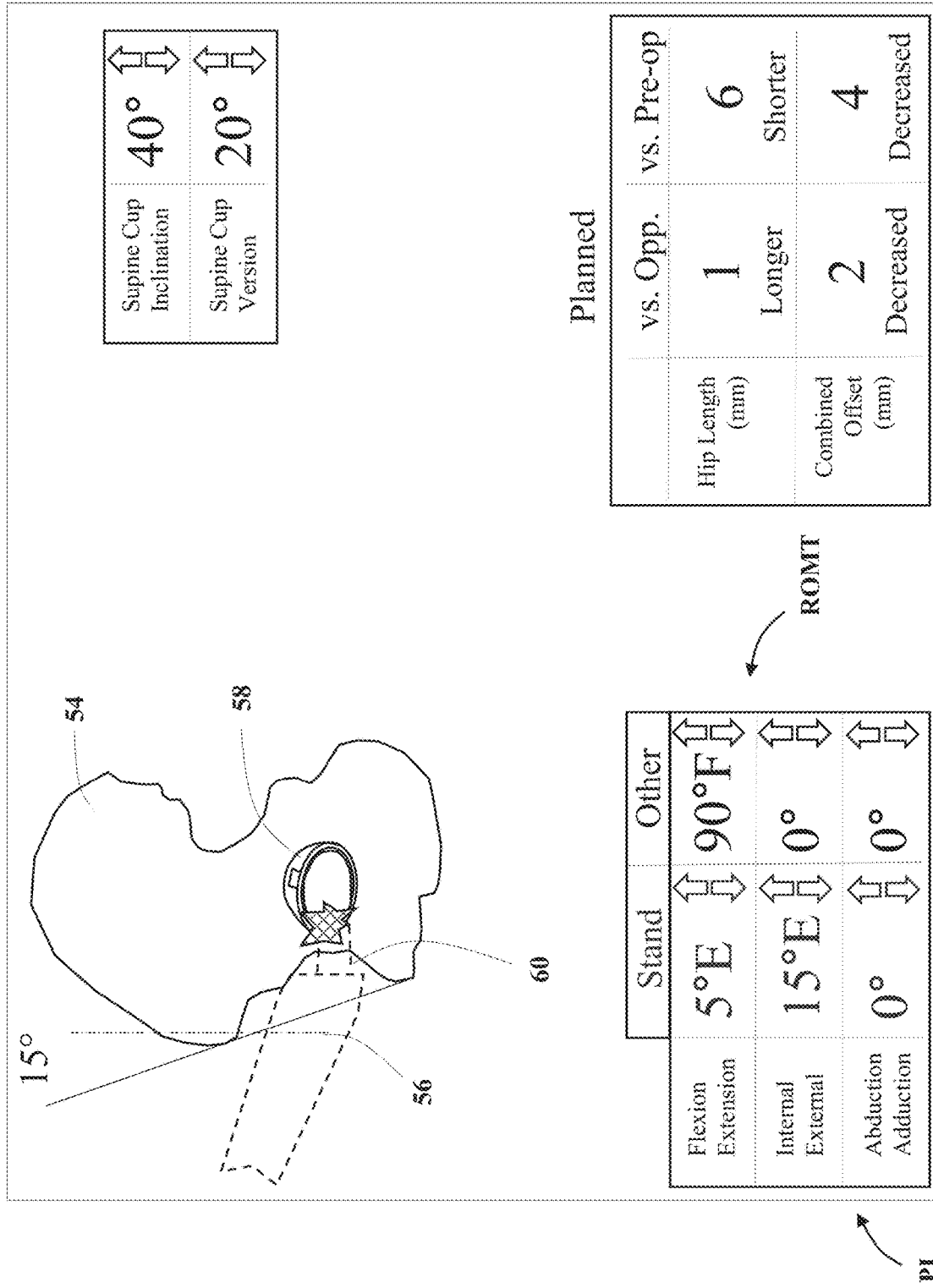
FIG. 18 shows the planning interface with a screen that illustrates impingement that occurs when the patient's anatomy is adjusted as shown in FIG. 17.

FIG. 16 shows the same screen as FIG. 14, but the pelvic tilt table PT has been updated to include a pelvic tilt angle θ for another functional position and associated values for the inclination angle γ and the version angle λ to enable ROM analysis for the other functional position, as shown in FIGS. 17 and 18, wherein FIG. 18 visually indicates impingement occurring as previously described. FIGS. 16-18 represent, for example, a pelvis PEL flexing anteriorly by 15° when the patient bends forward to get out of a chair or tie shoes, both movements that are associated with hip dislocation.

The ROM analysis can be conducted for the various functional positions by performing the analysis using the pelvic tilt angle θ measured for each of the functional positions, including the standing position, the seated position, the squat position, the bending position, or any other functional position. Thus, the planning controller 50 is operable to analyze a range-of-motion of the patient P based on the patient-specific data and identify any impingement of the stem implant SI on the acetabular implant AI. By knowing the pelvic tilt angle θ of the patient P in the various functional positions, the ROM analysis is greatly improved to account for variations in pelvic tilt relative to the supine position. As a result, users can more accurately consider how the implants AI, SI are positioned and move relative to each other when the patient P is moved to various functional positions. The user can then more accurately identify when impingements may occur and thus be able to refine placement of the acetabular implant AI to account for such potential impingements thereby customizing the placement of the acetabular implant AI based on the patient-specific data that is provided by the system 30.

In some versions, the user can utilize the measurements taken by the pelvic sensor 32 to better understand how the pelvic tilt angle θ for each patient changes between functional positions and/or during certain movements, and fine tune targets for the inclination angle γ and/or version angle λ to avoid impingement by employing the ROM evaluation methods described in U.S. Pat. No. 10,321,961, entitled "Patient Specific Implantation Method For Range Of Motion Hip Impingement," filed on Nov. 7, 2016, which is hereby incorporated herein by reference.

Figure 19:
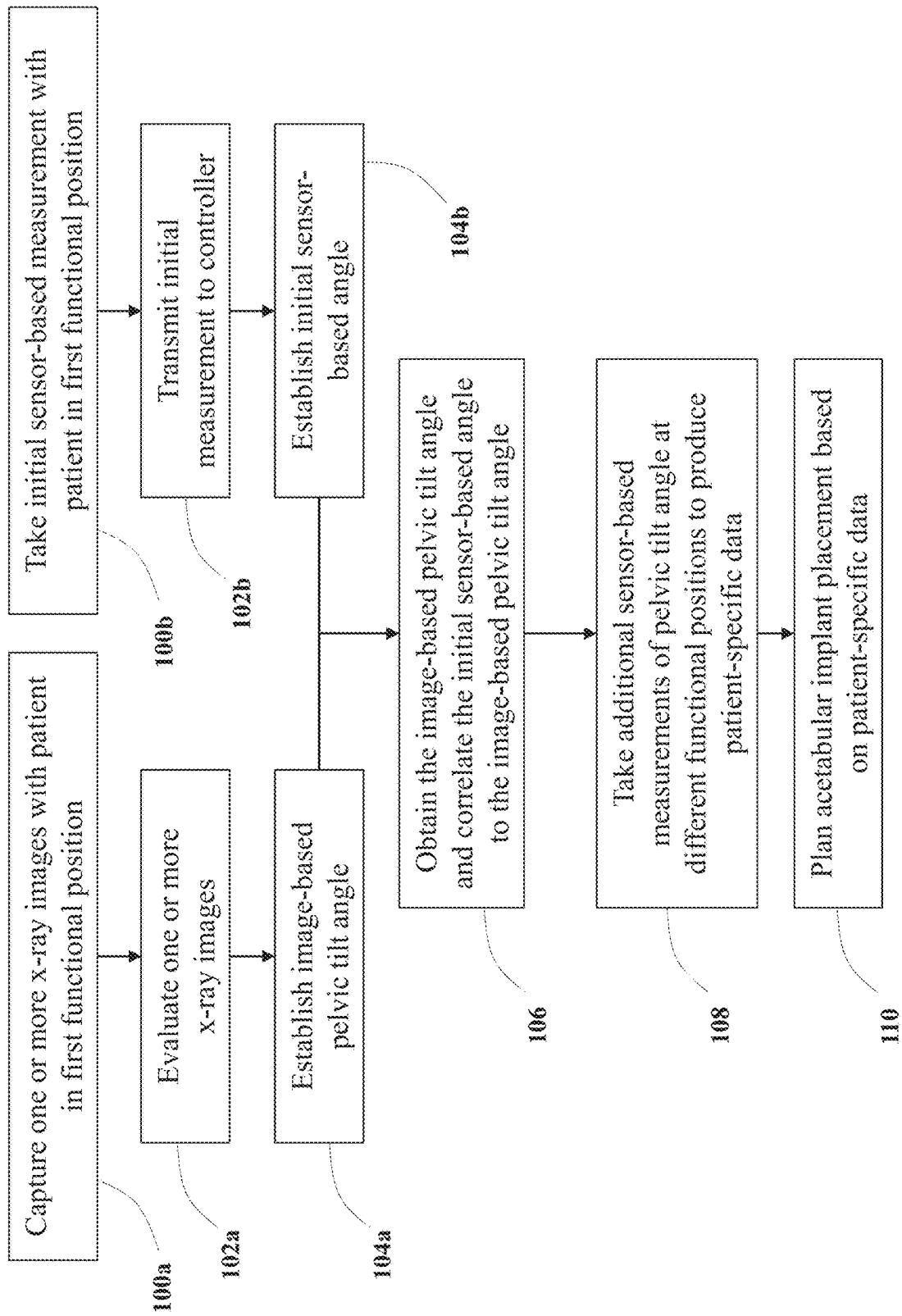
FIG. 19 is a flow chart of steps employed in some methods described herein.

Referring to FIG. 19, example steps performed when using the system 30 are shown. Initially, in step 100a, one or more x-ray images (e.g., a 2-D lateral x-ray image, a 2-D A/P x-ray image, x-ray images for a standing CT scan, and/or the like) are captured by an imaging device with the patient P in the first functional position (e.g., standing). This is performed pre-operatively and may be performed days or weeks ahead of the THA procedure. However, in some versions, this could be done intra-operatively. In step 100b, the pelvic sensor 32 takes the initial sensor-based measurement with the patient P in the same first functional position (e.g., standing). The initial sensor-based measurement includes measuring the initial sensor tilt angle ω1 between the y axis of the sensor body 34 of the pelvic sensor 32 and the gravity vector (g).

Steps 100a and 100b may be performed simultaneously, or substantially simultaneously, e.g., within less than 5 minutes of each other. For example, the user may first place the pelvic sensor 32 on the patient P via adhesive (or other attachment methods, such as using tape, bands, or straps), then position the patient P relative to the imaging device to take the one or more x-ray images. Once the patient P is in position relative to the imaging device, the initial sensor tilt angle ω1 can be measured and within 5 minutes, the one or more x-ray images can be taken, or vice versa. Of course, in some versions, steps 100a and 100b are not required to be performed simultaneously. If the patient P is in substantially the same functional position (e.g., standing) when the initial sensor-based measurement is taken and when the one or more x-ray images are captured, even though these events occur hours, days, or even weeks apart, the image-based pelvic tilt angle θ1 can still be correlated to the initial sensor tilt angle ω1, i.e., variation in the image-based pelvic tilt angle θ1 is likely to be negligible.

The one or more x-ray images are evaluated in step 102a after being transmitted to the image system (such as PACS) and/or the proprietary system along with other information that is associated with the one or more x-ray images such as a date/time that the one or more images were taken, the unique patient identification (ID), location/nature of the one or more x-ray images, technician that took the one or more x-ray images, the brand/model of the imaging device, etc. The imaging device may be connected to the image system (e.g., PACS) and/or the proprietary system via the network (Internet, etc.) so that the one or more x-ray images can be uploaded to the image system (e.g., PACS) and/or the proprietary system for later retrieval by the system 30. In step 102b, the initial sensor-based measurement (or measurements) are sent to the sensor controller 38, e.g., by wire or wirelessly.

In step 104a, the image-based pelvic tilt angle θ1 is established. This may be done using the image system, the proprietary system, and/or the sensor controller 38, and/or could be done manually, as previously described. In step 104b, the initial sensor tilt angle ω1 is established, for example, by the sensor controller 38 receiving the initial sensor tilt angle ω1 from the pelvic sensor 32, or by the sensor controller 38 calculating the initial sensor tilt angle ω1 based on readings from the pelvic sensor 32.

In step 106, the sensor controller 38 obtains the image-based pelvic tilt angle θ1 (e.g., from the image system, from the proprietary system, internally, from manual data entry, etc.) and correlates the initial sensor tilt angle ω1 to the image-based pelvic tilt angle θ1. Since the pelvic sensor 32 is initially placed without any reference to the actual position of the patient's pelvis PEL, measurements from the pelvic sensor 32, while in degrees, are likely not representative of the actual pelvic tilt angle θ. Thus, this step establishes a reference from which additional measurements can be made by the pelvic sensor 32 to yield patient-specific data corresponding to the actual pelvic tilt angle θ. Thereafter, in step 108, additional sensor-based measurements of the pelvic tilt angle θ can be taken, in the image-free mode, to produce patient-specific data. In step 110, the patient-specific data is used by the surgeon or others to plan placement of the acetabular implant AI, such as by using the patient-specific data in the surgical planning software in the manner described herein.

Using the one or more pelvic sensors 32 described herein to obtain patient-specific pelvic tilt data for various functional positions can occur much more quickly than capturing multiple x-ray images, and limits radiation exposure to the patient P. This can also save from higher costs normally associated with additional imaging and can be done in an office setting. In addition, multiple sessions of measuring pelvic tilt could be conducted with the pelvic sensors 32 very easily, and the patient P can be taken through functional positions and motions that cannot easily be captured with x-ray images. The system 30 and methods described herein can also be used as a screening process to help determine which patients may need additional x-ray images in order to perform enhanced THA pre-operative planning. For patients with spinal complexities, such as a stiff or hypermobile spine, advanced planning benefitted by additional x-ray images may be needed. However, it is difficult to determine which patients fall into this category without patient-specific data on pelvic motion. Instead of taking additional x-ray images on all patients, and only using the data from the additional x-ray images for the complex patients, the pelvic sensors 32 could be easily used to screen for the complex cases without additional x-ray images.

In some cases, the pelvic sensors 32 could be used for screening patients without initially capturing any x-ray images. For example, the pelvic sensor 32 may be employed to determine changes in the pelvic tilt angle θ (i.e., changes in the sensor tilt angle ω) between different functional positions, e.g., between standing and sitting positions. If the measured change represents normal pelvic movement, then the user/surgeon may decide that additional x-ray images are unnecessary and proceed to performing the total hip arthroplasty (THA) without any need to know the actual pelvic tilt angles θ for the patient as the patient represents a normal, non-complex case. However, if the measured change represents abnormal pelvic movement, this could indicate that there is a need to obtain the actual pelvic tilt angles θ to add to the software and on which to plan the total hip arthroplasty (THA). In this case, a 2-D x-ray image would be captured to determine the image-based pelvic tilt angle θ1 to correlate the sensor measurements to the actual pelvic tilt angles θ at each of the functional positions. Abnormal pelvic movement could be indicated, for example, if there was little change in the pelvic tilt angle θ between the different functional positions possibly due to a stiff spine brought on by osteoarthritis of the spinal region, or if there was a large change in the pelvic tilt angle θ due to the patient having a hypermobile spine/pelvis.

The foregoing description is merely illustrative in nature and is not intended to limit the disclosure, its application, or uses. The broad teachings of the disclosure can be implemented in a variety of forms or ways. Therefore, while this disclosure includes particular examples, the true scope of the disclosure should not be so limited since other modifications will become apparent upon a study of the drawings, the specification, and the following claims. It should be understood that one or more steps within a method may be executed in different order without altering the principles of the present disclosure. Further, although each of the examples is described above as having certain features, any one or more of those features described with respect to any example of the disclosure can be implemented in and/or combined with features of any of the other examples, even if that combination is not explicitly described. In other words, the described examples are not mutually exclusive, and permutations of one or more examples with one another remain within the scope of this disclosure.

Spatial and/or functional relationships between elements (for example, between controllers, etc.) are described using various terms, including "connected," "engaged," "coupled," "next to," "on top of," "above," "below," "adjacent," and "disposed." Unless explicitly described as being "direct," when a relationship between first and second elements is described in the above disclosure, that relationship can be a direct relationship where no other intervening elements are present between the first and second elements, but can also be an indirect relationship where one or more intervening elements are present (either spatially or functionally) between the first and second elements.

As may be used herein throughout the disclosure, the phrase at least one of A, B, and C should be construed to mean a logical (A OR B OR C), using a non-exclusive logical OR, and should not be construed to mean "at least one of A, at least one of B, and at least one of C." The term subset does not necessarily require a proper subset. In other words, a first subset of a first set may be coextensive with (equal to) the first set.

In the Figures, the direction of an arrow, as indicated by the arrowhead, may generally demonstrate the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application as may be used, including the definitions below, the term "controller" may be replaced with the term "circuit." The term "controller" may refer to, be part of, or include the following: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The controller may include one or more circuits, such as interface circuits. In some examples, the interface circuit(s) may implement wired or wireless (WIFI) interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

Each controller may communicate with one or more other controllers using the interface circuit(s). Although the controller may be depicted in the present disclosure as logically communicating directly with other controllers, in various configurations the controller may communicate via a communications system. The communications system includes physical and/or virtual networking equipment such as hubs, switches, routers, and gateways. In some configurations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various configurations, the functionality of the controller may be distributed among multiple controllers that are connected via the communications system. For example, multiple controllers may implement the same functionality in a distributed manner. In a further example, the functionality of the controller may be split between a server (also known as remote, or cloud) controller and a client (or, user) controller.

Some or all hardware features of a controller may be defined using a language for hardware description, such as IEEE Standard 1364-2005 (commonly called "Verilog") and IEEE Standard 10182-2008 (commonly called "VHDL"). The hardware description language may be used to manufacture and/or program a hardware circuit. In some configurations, some or all features of a controller may be defined by a language, such as IEEE 1666-2005 (commonly called "SystemC"), that encompasses both code, as described below, and hardware description.

The term code, as may be used above, may include software, firmware, and/or microcode, and may refer to programs, routines, functions, classes, data structures, and/or objects. The term shared processor circuit encompasses a single processor circuit that executes some or all code from multiple controllers. The term group processor circuit, as may be used above, encompasses a processor circuit that, in combination with additional processor circuits, executes some or all code from one or more controllers. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple controllers. The term group memory circuit, as may be used above, encompasses a memory circuit that, in combination with additional memories, stores some or all code from one or more controllers.

The term memory circuit, as may be used above, is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer application and/or programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SSENSORLINK, and Python®.

What is claimed is:

1. A system for planning placement of an acetabular implant for a patient based on pelvic tilt, the system comprising:
    a display;
    one or more sensors to be placed on the patient and operable to provide:
        a first measurement taken with the patient in a first functional position to establish an initial sensor tilt angle; and
        a second measurement taken, in an image-free mode, with the patient in a second functional position, different than the first functional position, to produce patient-specific data based on pelvic tilt from which to plan an inclination angle and a version angle of the acetabular implant for the patient; and
    a system controller operable to:
        establish an image-based pelvic tilt angle for the patient for the first functional position;
        correlate the initial sensor tilt angle to the image-based pelvic tilt angle,
        generate a representation of a virtual, three-dimensional bone model of the patient,
        display the representation of the virtual, three-dimensional bone model on the display, and
        display a representation of a virtual, three-dimensional model of the acetabular implant on the display.

2. The system of claim 1, wherein the first functional position is further defined as a standing position.

3. The system of claim 2, wherein the second functional position is further defined as a seated position, a squat position, or a bending position.

4. The system of claim 1, wherein the system controller is configured to correlate the initial sensor tilt angle to the image-based pelvic tilt angle by:
    setting the initial sensor tilt angle to the image-based pelvic tilt angle; or
    zeroing the initial sensor tilt angle such that the second measurement is relative to the image-based pelvic tilt angle.

5. The system of claim 4, wherein the system controller is configured to correlate the initial sensor tilt angle to the image-based pelvic tilt angle when the first measurement is taken substantially simultaneously with one or more x-ray images of the patient being captured to determine the image-based pelvic tilt angle.

6. The system of claim 4, wherein the system controller is configured to correlate the initial sensor tilt angle to the image-based pelvic tilt angle when the first measurement is taken at a time that is different than when one or more x-ray images of the patient are captured to determine the image-based pelvic tilt angle.

7. The system of claim 1, wherein the system controller is operable to establish the image-based pelvic tilt angle by one or more of: receiving the image-based pelvic tilt angle after being input by a user; retrieving the image-based pelvic tilt angle from memory; or measuring the image-based pelvic tilt angle on an image or model.

8. The system of claim 1, wherein the one or more sensors are operable to provide one or more additional measurements taken, in the image-free mode, and with the patient in one or more additional functional positions, different than the first and second functional positions.

9. The system of claim 1, wherein the one or more sensors are operable to provide a plurality of additional measurements taken, in the image-free mode, and while the patient moves through a plurality of functional positions to produce dynamic pelvic tilt data.

10. The system of claim 1, wherein the system controller is operable to determine whether the patient requires one or more x-ray images to be taken based on the second measurement.

11. The system of claim 1, wherein the one or more sensors are further defined as a pelvic sensor to be placed on a back of the patient, wherein the pelvic sensor includes an inertial measurement unit to measure a pelvic tilt angle of the patient.

12. The system of claim 1, wherein the system controller is operable to analyze a range of motion of the patient based on the patient-specific data and identify any impingement.

13. The system of claim 1, wherein the one or more sensors are operable to measure rotation of a patient.

14. The system of claim 13, wherein the one or more sensors are operable to measure twisting of a pelvis of the patient.

15. The system of claim 1, wherein the system controller is operable to establish the image-based pelvic tilt angle for the first functional position based on one or more x-ray images captured with the patient in the first functional position.

16. A method of planning placement of an acetabular implant for a patient based on pelvic tilt, the method comprising the steps of:
    establishing an image-based pelvic tilt angle for the patient for a first functional position;
    obtaining a first measurement provided by one or more sensors placed on the patient and taken with the patient in the first functional position to establish an initial sensor tilt angle;
    correlating the initial sensor tilt angle to the image-based pelvic tilt angle;
    obtaining a second measurement provided by the one or more sensors placed on the patient and taken, in an image-free mode, with the patient in a second functional position, different than the first functional position, to produce patient-specific data based on pelvic tilt from which to plan an inclination angle and a version angle of the acetabular implant for the patient;
    generating a representation of a virtual, three-dimensional bone model of the patient;
    displaying the representation of the virtual, three-dimensional bone model; and
    displaying a representation of a virtual, three-dimensional model of the acetabular implant.

17. The method of claim 16, wherein establishing the image-based pelvic tilt angle for the first functional position is further defined as establishing the image-based pelvic tilt angle for a standing position; and
    wherein obtaining the second measurement taken with the patient in the second functional position is further defined as obtaining the second measurement taken with the patient in a position other than the standing position.

18. The method of claim 16, wherein correlating the initial sensor tilt angle to the image-based pelvic tilt angle includes:
    setting the initial sensor tilt angle to the image-based pelvic tilt angle; or
    zeroing the initial sensor tilt angle such that the second measurement is relative to the image-based pelvic tilt angle; and
    wherein the first measurement is taken with the one or more sensors substantially simultaneously with capturing one or more x-ray images of the patient.

19. The method of claim 16, wherein correlating the initial sensor tilt angle to the image-based pelvic tilt angle includes:
    setting the initial sensor tilt angle to the image-based pelvic tilt angle; or
    zeroing the initial sensor tilt angle such that the second measurement is relative to the image-based pelvic tilt angle; and
    wherein the first measurement is taken with the one or more sensors at a time that is different than when capturing one or more x-ray images of the patient.

* * * * *